(12) United States Patent
Semizarov et al.

(10) Patent No.: US 8,498,820 B2
(45) Date of Patent: Jul. 30, 2013

(54) GENOMIC CLASSIFICATION OF NON-SMALL CELL LUNG CARCINOMA BASED ON PATTERNS OF GENE COPY NUMBER ALTERATIONS

(75) Inventors: Dimitri Semizarov, Chicago, IL (US); Xin Lu, Libertyville, IL (US); Ke Zhang, Grand Forks, ND (US); Rick R. Lesniewski, Collegeville, PA (US)

(73) Assignee: AbbVie Inc., North Chicago, IL (US)

( * ) Notice: Subject to any disclaimer, the term of this patent is extended or adjusted under 35 U.S.C. 154(b) by 370 days.

(21) Appl. No.: 12/607,079

(22) Filed: Oct. 28, 2009

(65) Prior Publication Data

US 2010/0145893 A1   Jun. 10, 2010

Related U.S. Application Data

(60) Provisional application No. 61/110,317, filed on Oct. 31, 2008, provisional application No. 61/110,281, filed on Oct. 31, 2008.

(51) Int. Cl.
| | |
|---|---|
| G01N 33/48 | (2006.01) |
| G01N 33/50 | (2006.01) |
| G01N 31/00 | (2006.01) |
| G06G 7/48 | (2006.01) |
| G06F 19/00 | (2011.01) |

(52) U.S. Cl.
CPC .................................... G06F 19/34 (2013.01)
USPC .................................. 702/19; 702/22; 703/3

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,889,818 | A | 12/1989 | Gelfand et al. |
| 5,143,854 | A | 9/1992 | Pirrung et al. |
| 5,310,652 | A | 5/1994 | Gelfand et al. |
| 5,322,770 | A | 6/1994 | Gelfand |
| 5,384,261 | A | 1/1995 | Winkler et al. |
| 5,424,186 | A | 6/1995 | Fodor et al. |
| 5,445,934 | A | 8/1995 | Fodor et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,789,162 | A | 8/1998 | Dower et al. |
| 5,800,992 | A | 9/1998 | Fodor et al. |
| 5,856,174 | A | 1/1999 | Lipshutz et al. |
| 5,922,591 | A | 7/1999 | Anderson et al. |
| 6,040,193 | A | 3/2000 | Winkler et al. |
| 2002/0068288 | A1 * | 6/2002 | Lodes et al. .................. 435/6 |
| 2005/0260586 | A1 * | 11/2005 | Demuth et al. ............... 435/6 |
| 2006/0195266 | A1 * | 8/2006 | Yeatman ..................... 702/19 |

OTHER PUBLICATIONS

Olejniczak et al. Molecular Cancer Research, Apr. 2007, vol. 5, pp. 331-339.*

(Continued)

*Primary Examiner* — Russell S Negin
(74) *Attorney, Agent, or Firm* — Lisa V. Mueller; Michael Best & Friedrich LLP

(57) ABSTRACT

The invention is directed to methods and kits that allow for classification of non-small cell lung carcinoma tumors and cell lines according to genomic profiles, and methods of diagnosing, predicting clinical outcomes, and stratifying patient populations for clinical testing and treatment using the same.

9 Claims, 7 Drawing Sheets

OTHER PUBLICATIONS

Anderson et al. Introduction to Statistics, Second Edition. New York: West Publishing Company, 1991, pp. 486-495.*

Craig et al. Proceedings of the Sixth Intervational Conference on Information Visualisation, 2002, 7 pages.*

Miozzi et al. PLoS ONE, Jun. 2008, vol. 3, e2439, 7 pages.*

Wolberg et al. Archives of Surgery, 1995, vol. 130, pp. 511-516.*

Anand S., et al., "AURORA-A Amplification Overrides the Mitotic Spindle Assembly Checkpoint, Inducing Resistance to Taxol," Cancer Cell, 2003, vol. 3 (1), pp. 51-62.

Ausubel F.M., et al., eds., Current Protocols in Molecular Biology, vol. 1, John Wiley & Sons Inc., 1994, Table of Contents.

Bhattacharjee A., et al., "Classification of Human Lung Carcinomas by mRNA Expression Profiling Reveals Distinct Adenocarcinoma Subclasses," Proceedings of the National Academy of Sciences, 2001, vol. 98 (24), pp. 13790-13795.

Borg I., et al., "Modern Multidimensional Scaling," in: Springer Series in Statistics, 2nd Edition, Springer Verlag, 2005, Table of Contents.

Breiman L., "Random Forests," Machine Learning, 2001, vol. 45, pp. 5-32.

Brunet J.P., et al., "Metagenes and Molecular Pattern Discovery Using Matrix Factorization," Proceedings of the National Academy of Sciences, 2004, vol. 101 (12), pp. 4164-4169.

Carrasco D.R., et al., "High-resolution Genomic Profiles Define Distinct Clinico-Pathogenetic Subgroups of Multiple Myeloma Patients," Cancer Cell, 2006, vol. 9 (4), pp. 313-325.

Clegg A., et al., "Clinical and Cost Effectiveness of Paclitaxel, Docetaxel, Gemcitabine, and Vinorelbine in Non-Small Cell Lung Cancer: A Systematic Review," Thorax, 2002, vol. 57 (1), pp. 20-28.

Efron B., et al., "Least Angle Regression," The Annals of Statistics, 2004, vol. 32 (2), pp. 407-499.

Fodor S.P.A., et al., "Light-Directed, Spatially Addressable Parallel Chemical Synthesis," Science, 1991, vol. 251 (4995), pp. 767-773.

Fridlyand J., et al., "Hidden Markov Models Approach to the Analysis of Array CGH Data," Journal of Multivariate Analysis, 2004, vol. 90, pp. 132-153.

Hedenfalk I., et al., "Molecular Classification of Familial Non-BRCA1/BRCA2 Breast Cancer," Proceedings of the National Academy of Sciences, 2003, vol. 100 (5), pp. 2532-2537.

Hirsch F.R., et al., "Molecular Predictors of Outcome With Gefitinib in a Phase III Placebo-Controlled Study in Advanced Non-Small-Cell Lung Cancer," Journal of Clinical Oncology, 2006, vol. 24 (31), pp. 5034-5042.

Hodgson G., et al., "Genome Scanning with Array CGH Delineates Regional Alterations in Mouse Islet Carcinomas," Nature Genetics, 2001, vol. 29 (4), pp. 459-464.

Hoffman P.C., et al., "Lung Cancer," Lancet, 2000, vol. 355, pp. 479-485.

Holland P.M., et al., "Detection of Specific Polymerase Chain Reaction Product by Utilizing the 5' → 3' Exonuclease Activity of *Thermus aquaticus* DNA Polymerase," Proceedings of the National Academy of Sciences, 1991, vol. 88, pp. 7276-7280.

Hupe P., et al., "Analysis of Array CGH Data: From Signal Ratio to Gain and Loss of DNA Regions," Bioinformatics, 2004, vol. 20 (18), pp. 3413-3422.

Innis M.A., et al., eds., "A Guide to Methods and Applications," in: PCR Protocols, Academic Press Inc., 1990, Table of Contents.

Innis M.A., et al., eds., PCR Strategies, Academic Press Inc., 1995, Table of Contents.

Innis M.A., et al., eds., "Protocols for Functional Genomics" in: PCR Applications, Academic Press Inc., 1999, Table of Contents.

Lee D.D., et al., "Algorithms for Non-Negative Matrix Factorization," Advances in Neural Information Processing Systems, 2000, vol. 13, pp. 556.

Lee D.D., et al., "Learning the Parts of Objects by Non-Negative Matrix Factorization," Nature, 1999, vol. 401, pp. 788-791.

Levsky J.M., et al., "Fluorescence in Situ Hybridization: Past, Present and Future," Journal of Cell Science, 2003, vol. 116 (Pt 14), pp. 2833-2838.

Li C., et al., "Model-based Analysis of Oligonucleotide Arrays: Expression Index Computation and Outlier Detection," Proceedings of the National Academy of Sciences, 2001, vol. 98 (1), pp. 31-36.

Li C., et al., "Model-based Analysis of Oligonucleotide Arrays: Model Validation, Design Issues and Standard Error Application, Research/0032.1," Genome Biology, 2001, vol. 2 (8), pp. Research0032.1-Research0032.11.

Maher E.A., et al., "Marked Genomic Differences Characterize Primary and Secondary Glioblastoma Subtypes and Identify Two Distinct Molecular and Clinical Secondary Glioblastoma Entities," Cancer Research, 2006, vol. 66 (23), pp. 11502-11513.

Matsuzaki H., et al., "Genotyping Over 100,000 SNPs on a Pair of Oligonucleotide Arrays," Nature Methods, 2004, vol. 1 (2), pp. 109-111.

McPherson M.J., et al., PCR: A Practical Approach, Oxford University Press, 1991, Table of Contents.

Olshen A.B., et al., "Circular Binary Segmentation for the Analysis of Array-based DNA Copy Number Data," Biostatistics, 2004, vol. 5 (4), pp. 557-572.

Parkin D.M., "Global Cancer Statistics in the Year 2000," The Lancet Oncology, 2001, vol. 2, pp. 533-543.

Pearson K., et al., "On Lines and Planes of Closest Fit to Systems of Points in Space," Philosophical Magazine, 1901, vol. 2 (11), pp. 559-572.

Reich M., et al., "GenePattern 2.0," Nature Genetics, 2006, vol. 38 (5), pp. 500-501.

Ross D.T., et al., "Systematic Variation in Gene Expression Patterns in Human Cancer Cell Lines," Nature Genetics, 2000, vol. 24, pp. 227-235.

Saiki R.K., et al., "Analysis of Enzymatically Amplified β-Globin and HLA-DQα DNA with Allele-Specific Oligonucleotide Probes," Nature, 1986, vol. 324, pp. 163-166.

Sambrook J., et al., eds., Molecular Cloning: A Laboratory Manual, 3rd Edition, Cold Spring Harbor Laboratory, 2001, Table of Contents.

Schwarz G., "Estimating the Dimension of a Model," Annals of Statistics, 1978, vol. 6 (2), pp. 461-464.

Seeger R.C., et al., "Association of Multiple Copies of the N-myc Oncogene with Rapid Progression of Neuroblastomas," The New England Journal of Medicine, 1985, vol. 313 (18), pp. 1111-1116.

Sotiriou C., et al., "Breast Cancer Classification and Prognosis Based on Gene Expression Profiles From a Population-Based Study," Proceedings of the National Academy of Sciences, 2003, vol. 100 (18), pp. 10393-10398.

Travis W.D., et al., "Histological Typing of Lung and Pleural Tumours," 3rd Edition, Springer Verlag, 1999, Table of Contents.

Vapnik V.N., "The Nature of Statistical Learning Theory," Springer Verlag, 1995, Table of Contents.

Vogel C.L., et al., "Efficacy and Safety of Trastuzumab as a Single Agent in First-Line Treatment of HER2-Overexpressing Metastatic Breast Cancer," Journal of Clinical Oncology, 2002, vol. 20 (3), pp. 719-726.

Wang P., et al., "A Method for Calling Gains and Losses in Array CGH Data," Biostatistics, 2005, vol. 6 (1), pp. 45-58.

Wilhelm M., et al., "Array-Based Comparative Genomic Hybridization for the Differential Diagnosis of Renal Cell Cancer," Cancer Research, 2002, vol. 62 (4), pp. 957-960.

Zhang X., et al., "Recursive SVM Feature Selection and Sample Classification for Mass-Spectrometry and Microarray Data," BMC Bioinformatics, 2006, vol. 7, pp. 197.

Zhao X., et al., "An Integrated View of Copy Number and Allelic Alterations in the Cancer Genome Using Single Nucleotide Polymorphism Arrays," Cancer Research, 2004, vol. 64, pp. 3060-3071.

Zhao X., et al., "Homozygous Deletions and Chromosome Amplifications in Human Lung Carcinomas Revealed by Single Nucleotide Polymorphism Array Analysis," Cancer Research, 2005, vol. 65 (13), pp. 5561-5570.

\* cited by examiner

GENOMIC CLASSIFICATION OF NON-SMALL CELL LUNG CARCINOMA BASED ON PATTERNS OF GENE COPY NUMBER ALTERATIONS

CROSS-REFERENCE TO RELATED APPLICATIONS

This application claims priority to U.S. Application No. 61/110,317 filed on Oct. 31, 2008, the contents of which are herein incorporated by reference.

This application also incorporates by reference the application entitled METHODS FOR ASSEMBLING PANELS OF CANCER CELL LINES FOR USE IN TESTING THE EFFICACY OF ONE OR MORE PHARMACEUTICAL COMPOSITIONS, (Dimitri Semizarov, Xin Lu, Ke Zhang, and Rick Lesniewski, inventors; filed on Oct. 28, 2009, which claims priority to U.S. Application No. 61/110,281 filed on Oct. 31, 2008).

STATEMENT REGARDING FEDERALLY SPONSORED RESEARCH OR DEVELOPMENT

Not applicable.

REFERENCE TO MATERIAL ON A COMPACT DISC

Not applicable.

SEQUENCE LISTING

The instant application contains a Sequence Listing which has been submitted via EFS-Web and is hereby incorporated by reference in its entirety. Said ASCII copy, created on Oct. 27, 2009, is named 9670USO1.txt, and is 1,110 bytes in size.

BACKGROUND OF THE INVENTION

1. Field of the Invention

The present invention relates to methods for defining genomic subgroups of tumors, cancer cell lines and subject samples related to non-small cell lung carcinoma (NSCLC). The present invention also relates to methods for assembling panels of tumors, cancer cell lines and subject samples according to genomic subgroups for use in testing the efficacy of one or more therapeutic interventions for administering to a subject.

2. Description of Related Art

Cancer is a disease of the genome characterized by substantial variability in clinical course, outcome, and therapy responsiveness. The main factor underlying this variability is the genetic heterogeneity innate to cancers. Individual tumors of the same histopathological subtype carry different aberrations in cellular DNA.

NSCLC is the most common cause of cancer-induced mortality worldwide (Parkin, 2001). Currently, NSCLC is characterized by histology—visual inspection of cell anatomy under a microscope, often coupled with various staining procedures to highlight specific physical characteristics of the cells. The major histologic subtypes of NSCLC are adenocarcinomas (the most common form of lung cancer), squamous cell lung carcinomas (SQ), and large-cell lung carcinomas (LCLC) (Travis and Sobin, 1999). About 40% of patients with early-stage NSCLC relapse within five years after surgical removal of the tumor {Hoffman, 2000 #39}. Current therapeutics for treating NSCLC are efficacious only in a fraction of patients, highlighting the fact that NSCLCs differ from each other. Tumors within the same histopathological groups follow significantly different clinical courses and respond differently to therapy. The current histology-based staging of NSCLC is therefore inadequate for predicting the clinical course of the disease or treatment outcome.

The phenotypic diversity of lung tumors is accompanied by a corresponding diversity in gene copy number aberration patterns. Chromosomal aberrations are detrimental events associated with a number of developmental diseases and cancer. Chromosomal region amplifications and deletions in somatic cells are believed to be one of the main factors leading to cancer. Systematic examination of gene copy number patterns in lung cancer might then serve as a foundation for a genomics-based molecular taxonomy of lung cancers. Recurrent chromosomal aberration of prognostic significance can be detected individually by classical cytogenetic analysis or fluorescent in situ hybridization (FISH) (Levsky and Singer, 2003). However, FISH analysis cannot detect the entire spectrum of genetic abnormalities as it only interrogates a limited set of chromosomal loci defined by the applied probe panel. A more advantageous diagnostic tool would be based on a refined classification of the disease. It would enable rational patient selection for treatment based on the genetic status of a subject's NSCLC.

BRIEF SUMMARY OF THE INVENTION

In a first aspect, the invention is directed to methods for obtaining a database of non-small cell lung carcinoma genomic subgroups, the method comprising the steps of:

(a) obtaining a plurality of m samples comprising at least one NSCLC cell, wherein the samples comprise cell lines or tumors;

(b) acquiring a data set comprising copy number alteration information from at least one locus from each chromosome from each sample obtained in step (a);

(c) identifying in the data set samples contaminated by normal cells and eliminating the contaminated samples from the data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the data set for each sample scoring 50% or greater probability of containing normal cells;

(d) estimating a number of subgroups, r, in the data set by applying an unsupervised clustering algorithm using Pearson linear dissimilarity algorithm to the data set;

(e) assigning each sample in the data set to at least one cluster using a modified genomic Non-negative Matrix Factorization (gNMF) algorithm, wherein the modified gNMF algorithm comprises:

(1) calculating divergence of the algorithm after every 100 steps of multiplicative updating using formula (11):

$$D(V \| WH) = \sum_{i=1}^{n} \sum_{j=1}^{m} \left( V_{ij} \log \frac{V_{ij}}{(WH)_{ij}} - V_{ij} + (WH)_{ij} \right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

(2) stopping the algorithm if the divergence calculated in step (e) (1) does not decrease by more than about 0.001% when compared to the divergence calculated for the previous 100 steps of multiplicative updating of the algorithm;

(3) randomly repeating the algorithm for a selected number of runs and calculating a Pearson correlation coefficient matrix of H for the each of run the algorithm using formula (12):

$$C_{i,j} = \rho(H_{,i}, H_{,j}) = \frac{\frac{1}{r-1}\sum_{k}(H_{k,i} - \overline{H_{,i}})(H_{k,j} - \overline{H_{,j}})}{s_{H_{,i}}s_{H_{,j}}} \quad (12)$$

wherein C is the correlation matrix, $C_{i,j}$ is the $i^{th}$ row and $j^{th}$ column in the matrix C, and $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups from step (d);

(4) averaging the Pearson correlation coefficient matrices for each run of the algorithm obtained from step (e)(3) to arrive at an average correlation matrix;

(5) assigning samples into r subgroups by applying a unsupervised clustering algorithm using 1 minus the average correlation matrix determined in step (e) (4) and cutting the dendrogram into r clusters;

(f) applying a Cophenetic correlation, Bayesian Information Criterion, or a combination thereof to provide a final number of clusters from the data set, wherein each final cluster defines a genomic subgroup for each tumor or cell line sample; and (g) optionally evaluating the stability of the final number of clusters selected in step (f) using a ten-fold stability test.

In a second aspect, the invention is directed to methods of classifying a NSCLC tumor or cell line, comprising:

(a) providing a database, developed through a method comprising:
(i) obtaining a plurality of m samples comprising at least one NSCLC tumor or cell line;
(ii) acquiring a first data set comprising copy number alteration information from at least one locus from each chromosome from each sample obtained in step (i);
(iii) identifying in the first data set samples contaminated by normal cells and eliminating the contaminated samples from the first data set, wherein the identifying and eliminating comprises:
(1) applying a machine learning algorithm tuned to parameters that represent the differences between tumor and normal samples to the data;
(2) assigning a probability score for normal cell contamination to each sample as determined by the machine learning algorithm;
(3) eliminating data from the first data set for each sample scoring 50% or greater probability of containing normal cells;
(iv) estimating a number of subgroups, r, in the data set by applying an unsupervised clustering algorithm using Pearson linear dissimilarity algorithm to the data set;
(v) assigning each sample in the data set to at least one cluster using a modified genomic Non-negative Matrix Factorization (gNMF) algorithm, wherein the modified gNMF algorithm comprises:
(1) calculating divergence of the algorithm after every 100 steps of multiplicative updating using formula (11):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set;

(2) stopping the algorithm if the divergence calculated in step (v)(1) does not decrease by more than about 0.001% when compared to the divergence calculated for the previous 100 steps of multiplicative updating of the algorithm;

(3) randomly repeating the algorithm for a selected number of runs and calculating a Pearson correlation coefficient matrix of H for each of run the algorithm using formula (12):

$$C_{i,j} = \rho(H_{,i}, H_{,j}) = \frac{\frac{1}{r-1}\sum_{k}(H_{k,i} - \overline{H_{,i}})(H_{k,j} - \overline{H_{,j}})}{s_{H_{,i}}s_{H_{,j}}} \quad (12)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups from step (iv);

(4) averaging the Pearson correlation coefficient matrices for each run of the algorithm obtained from step (v)(3) to arrive at an average correlation matrix;

(5) assigning tumors and cell lines in the data set into r subgroups by applying a unsupervised clustering algorithm using 1 minus the average correlation matrix determined in step (v)(4) and cutting the dendrogram into r clusters;

(vi) applying a Cophenetic correlation, Bayesian Information Criterion, or a combination thereof to provide a final number of clusters from the data set, wherein each final cluster defines a genomic subgroup for each sample; and (vii) optionally evaluating the stability of the final number of clusters selected in step (vi) using a ten-fold stability test;

(b) providing a sample suspected of containing NSCLC cells, (c) acquiring a second data set, Vsample, comprising copy number alteration information from the same at least one locus from step (ii); and (d) classifying the sample from Vsample, by comparing Vsample to the clusters determined in steps (i)-(vii).

In a third aspect, the invention is directed to methods of classifying a therapeutic intervention for arresting or killing non-small cell lung carcinoma (NSCLC) cells, comprising:

(a) from a panel of NSCLC cells classified according to genomic subgroups, selecting at least one NSCLS cell line from each subgroup, wherein the panel is assembled from a method comprising:

(i) obtaining a plurality of m samples comprising at least one NSCLC tumor or cell line;

(ii) acquiring a first data set comprising copy number alteration information from at least one locus from each chromosome from each sample obtained in step (i);

(iii) identifying in the first data set samples contaminated by normal cells and eliminating the contaminated samples from the first data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the first data set for each sample scoring 50% or greater probability of containing normal cells;

(iv) estimating a number of subgroups, r, in the data set by applying an unsupervised clustering algorithm using Pearson linear dissimilarity algorithm to the data set;

(v) assigning each sample in the data set to at least one cluster using a modified genomic Non-negative Matrix Factorization (gNMF) algorithm, wherein the modified gNMF algorithm comprises:

(1) calculating divergence of the algorithm after every 100 steps of multiplicative updating using formula (11):

$$D(V \| WH) = \sum_{i=1}^{n} \sum_{j=1}^{m} \left( V_{ij} \log \frac{V_{ij}}{(WH)_{ij}} - V_{ij} + (WH)_{ij} \right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set;

(2) stopping the algorithm if the divergence calculated in step (v)(1) does not decrease by more than about 0.001% when compared to the divergence calculated for the previous 100 steps of multiplicative updating of the algorithm;

(3) randomly repeating the algorithm for a selected number of runs and calculating a Pearson correlation coefficient matrix of H for each of run the algorithm using formula (12):

$$C_{i,j} = \rho(H_{,i}, H_{,j}) = \frac{\frac{1}{r-1} \sum_{k} (H_{k,i} - \overline{H_{,i}})(H_{k,j} - \overline{H_{,j}})}{s_{H_{,i}} s_{H_{,j}}} \quad (12)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups from step (iv);

(4) averaging the Pearson correlation coefficient matrices for each run of the algorithm obtained from step (v)(3) to arrive at an average correlation matrix;

(5) assigning tumors and cell lines in the data set into r subgroups by applying a unsupervised clustering algorithm using 1 minus the average correlation matrix determined in step (v)(4) and cutting the dendrogram into r clusters;

(vi) applying a Cophenetic correlation, Bayesian Information Criterion, or a combination thereof to provide a final number of clusters from the data set, wherein each final cluster defines a genomic subgroup for each sample; and (vii) optionally evaluating the stability of the final number of clusters selected in step (vi) using a ten-fold stability test (viii) selecting at least one NSCLC cell from each cluster selected in step (vi) and assembling into panels defined according to genomic subgroups.

(b) contacting the at least one NSCLC cell from each subgroup with the therapeutic intervention;

(c) assaying the effectiveness of the therapeutic intervention to arrest or kill the at least one NSCLC cell from each subgroup;

(d) classifying the therapeutic intervention according to the determined effectiveness of the therapeutic intervention to arrest or kill the at least one NSCLC cell from each subgroup, wherein arresting or killing the at least one NSCLC cell from one subgroup, but not another indicates specificity of the therapeutic intervention to arrest or kill NSCLC cells of that subgroup. The therapeutic intervention can be radiation therapy, chemotherapy, laser therapy, photodynamic, and biologic therapy. If the therapeutic intervention is chemotherapy, the chemotherapy can comprise administering at least one pharmaceutical composition comprising an active agent selected from the group consisting of alimta, erlotinib, gefitinib, cisplatin, gemcitabine, paclitaxel, vinorelbine, epirubicin, vindesine, lonidamine, ifosfamide, carboplatin, and docetaxel and ifosfamide. Chemotherapy can comprise administering two or more active agents.

In a fourth aspect, the invention is directed to methods of assembling a probe panel for classifying a NSCLC cell from a sample, comprising:

(a) assembling a database, comprising:

(i) obtaining a plurality of m samples comprising at least one NSCLC tumor or cell line;

(ii) acquiring a first data set comprising copy number alteration information from at least one locus from each chromosome from each sample obtained in step (i);

(iii) identifying in the first data set samples contaminated by normal cells and eliminating the contaminated samples from the first data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the first data set for each sample scoring 50% or greater probability of containing normal cells;

(iv) estimating a number of subgroups, r, in the data set by applying an unsupervised clustering algorithm using Pearson linear dissimilarity algorithm to the data set;

(v) assigning each sample in the data set to at least one cluster using a modified genomic Non-negative Matrix Factorization (gNMF) algorithm, wherein the modified gNMF algorithm comprises:
(1) calculating divergence of the algorithm after every 100 steps of multiplicative updating using formula (11):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set;
(2) stopping the algorithm if the divergence calculated in step (v)(1) does not decrease by more than about 0.001% when compared to the divergence calculated for the previous 100 steps of multiplicative updating of the algorithm;
(3) randomly repeating the algorithm for a selected number of runs and calculating a Pearson correlation coefficient matrix of H for each of run the algorithm using formula (12):

$$C_{i,j} = \rho(H_{,i}, H_{,j}) = \frac{\frac{1}{r-1}\sum_{k}(H_{k,i} - \overline{H_{,i}})(H_{k,j} - \overline{H_{,j}})}{s_{H_{,i}}s_{H_{,j}}} \quad (12)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups from step (iv);
(4) averaging the Pearson correlation coefficient matrices for each run of the algorithm obtained from step (v)(3) to arrive at an average correlation matrix;
(5) assigning tumors and cell lines in the data set into r subgroups by applying a unsupervised clustering algorithm using 1 minus the average correlation matrix determined in step (v)(4) and cutting the dendrogram into r clusters;
(vi) applying a Cophenetic correlation, Bayesian Information Criterion, or a combination thereof to provide a final number of clusters from the data set, wherein each final cluster defines a genomic subgroup for each sample; and
(vii) optionally evaluating the stability of the final number of clusters selected in step (vi) using a ten-fold stability test
(viii) selecting at least one sample from each cluster selected in step (vi) and assembling into panels defined according to genomic subgroups;
(b) analyzing the database of step (a) to determine characteristic copy number abnormalities for each subgroup;
(c) designing a plurality of probes based on the determined characteristic copy number abnormalities for each subgroup and assigning each probe to a genomic subgroup.
In a fifth aspect, the invention is directed to kits comprising a probe panel for classifying an NSCLC tumor sample. The probes in the probe panel can be, for example, FISH probes.

In a sixth aspect, the invention is directed to kits for classifying a NSCLC tumor sample, comprising:
(a) instructions to assemble a database, comprising instructions for:
(i) obtaining a plurality of m samples comprising at least one NSCLC tumor or cell line;
(ii) acquiring a first data set comprising copy number alteration information from at least one locus from each chromosome from each sample obtained in step (i);
(iii) identifying in the first data set samples contaminated by normal cells and eliminating the contaminated samples from the first data set, wherein the identifying and eliminating comprises:
(1) applying a machine learning algorithm tuned to parameters that represent the differences between tumor and normal samples to the data;
(2) assigning a probability score for normal cell contamination to each sample as determined by the machine learning algorithm;
(3) eliminating data from the first data set for each sample scoring 50% or greater probability of containing normal cells;
(iv) estimating a number of subgroups, r, in the data set by applying an unsupervised clustering algorithm using Pearson linear dissimilarity algorithm to the data set;
(v) assigning each sample in the data set to at least one cluster using a modified genomic Non-negative Matrix Factorization (gNMF) algorithm, wherein the modified gNMF algorithm comprises:
(1) calculating divergence of the algorithm after every 100 steps of multiplicative updating using formula (11):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set;
(2) stopping the algorithm if the divergence calculated in step (v)(1) does not decrease by more than about 0.001% when compared to the divergence calculated for the previous 100 steps of multiplicative updating of the algorithm;
(3) randomly repeating the algorithm for a selected number of runs and calculating a Pearson correlation coefficient matrix of H for each of run the algorithm using formula (12):

$$C_{i,j} = \rho(H_{,i}, H_{,j}) = \frac{\frac{1}{r-1}\sum_{k}(H_{k,i} - \overline{H_{,i}})(H_{k,j} - \overline{H_{,j}})}{s_{H_{,i}}s_{H_{,j}}} \quad (12)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between and $H_{,i}$ and $H_{,j}$, i and j run from 1 to m and m is the number of samples in the data set, k runs from 1 to r and r is the number of subgroups from step (iv);

(4) averaging the Pearson correlation coefficient matrices for each run of the algorithm obtained from step (v)(3) to arrive at an average correlation matrix;

(5) assigning tumors and cell lines in the data set into r subgroups by applying a unsupervised clustering algorithm using 1 minus the average correlation matrix determined in step (v)(4) and cutting the dendrogram into r clusters;

(vi) applying a Cophenetic correlation, Bayesian Information Criterion, or a combination thereof to provide a final number of clusters from the data set, wherein each final cluster defines a genomic subgroup for each sample; and (vii) optionally evaluating the stability of the final number of clusters selected in step (vi) using a ten-fold stability test; and (b) optionally, a first, second and third cell line, or isolated genomic DNA thereof, wherein the first cell line is selected from the group consisting of HCC827, NCI-H1437, NCI-H1563, NCI-H1568, NCI-H1623, NCI-H1651, NCI-H1693, NCI-H1755, NCI-H1793, NCI-H1838, NCI-H1944, NCI-H1975, NCI-H1993, NCI-H2023, NCI-H2073, NCI-H2085, NCI-H2087, NCI-H2122, NCI-H2126, NCI-H2228, NCI-H2291, NCI-H23, NCI-H2342, NCI-H2347, NCI-H647, NCI-H920, NCI-H969, CLS-54, LX-289, SK-LU-1, H2882, Calu-6, H358, and H460;

the second cell line is selected from the group consisting of NCI-H2405, NCI-H522, SK-MES-1, H157, H1819, H2009, H2887, HCC1171, HCC1359, HCC15, HCC193, HCC366, HCC461, HCC515, HCC78, HOP-62, HOP-92, and NCI-H266; and the third cell line is selected from the group consisting of A549, Calu-3, NCI-H1734, NCI-H838, and HCC95.

In all aspects of the invention, the unsupervised clustering algorithm can be hierarchical clustering, Cophenetic correlation or Bayesian Information Criterion can be used, independently or together, to provide a final number of clusters from the data set.

In all aspects of the invention, the plurality of samples, m, can comprise a first, second, and third cell line, wherein the first cell line is selected from the group consisting of HCC827, NCI-H1437, NCI-H1563, NCI-H1568, NCI-H1623, NCI-H1651, NCI-H1693, NCI-H1755, NCI-H1793, NCI-H1838, NCI-H1944, NCI-H1975, NCI-H1993, NCI-H2023, NCI-H2073, NCI-H2085, NCI-H2087, NCI-H2122, NCI-H2126, NCI-H2228, NCI-H2291, NCI-H23, NCI-H2342, NCI-H2347, NCI-H647, NCI-H920, NCI-H969, CLS-54, LX-289, SK-LU-1, H2882, Calu-6, H358, and H460;

the second cell line is selected from the group consisting of NCI-H2405, NCI-H522, SK-MES-1, H157, H1819, H2009, H2887, HCC1171, HCC1359, HCC15, HCC193, HCC366, HCC461, HCC515, HCC78, HOP-62, HOP-92, and NCI-H266; and the third cell line is selected from the group consisting of A549, Calu-3, NCI-H1734, NCI-H838, and HCC95. In some aspects, m comprises all the afore-mentioned cell lines.

In some aspects of the invention, the NSCLC cells are from cell lines.

DETAILED DESCRIPTION OF THE INVENTION

Figure 1:
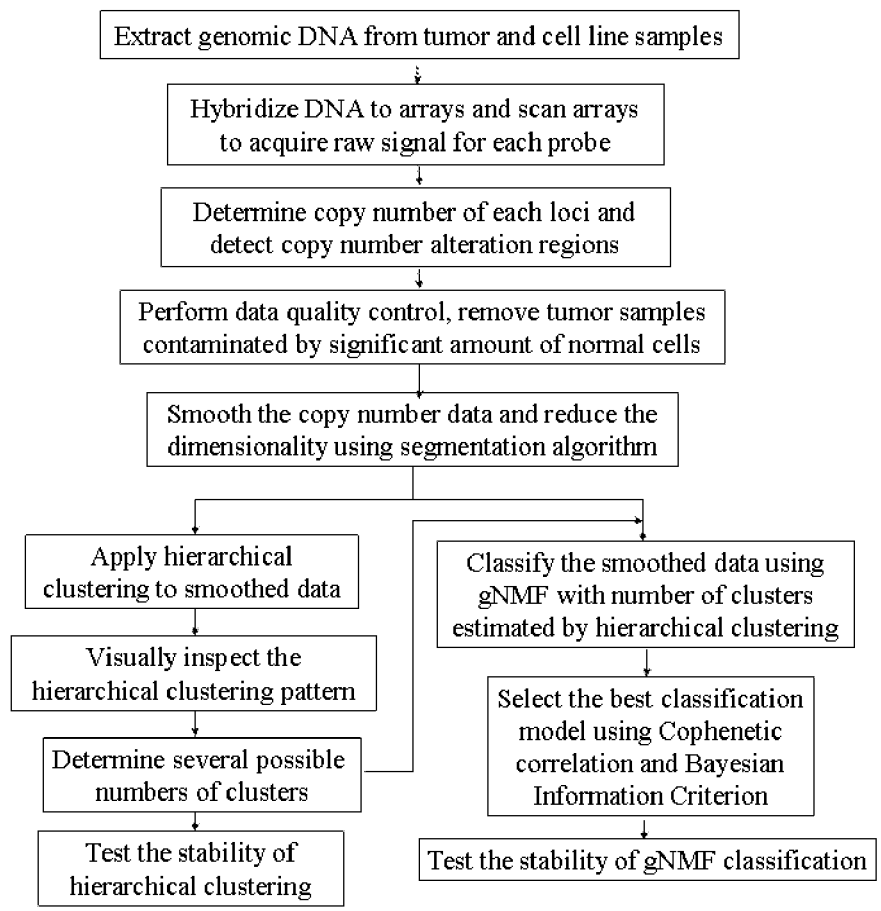
FIG. 1 shows a workflow of the genomics-based tumor classification procedure

The invention provides for assessing, classifying and stratifying NSCLC tumors, as well as evaluating therapeutic intervention efficacy for NSCLC tumors. The invention exploits microarray-based comparative genomic hybridization techniques to detect gene copy number abnormalities on a genome-wide scale, thus providing a whole-genome view of chromosomal aberrations accompanied by a change in the DNA copy number. Unlike previous histopathology-based classification schemes, the methods of the invention ascertain the genetic heterogeneity of NSCLC cells, the main factor behind the observed variability in clinical interventions.

The methods of the invention allow for genomic subgrouping of NSCLC to facilitate discovery and development of targeted therapies against NSCLC, as well as for defining discrete patient populations who harbor NSCLCs that would be susceptible to these therapies. This stratification of patient groups is also extraordinarily useful in clinical trial design.

The subgroups defined by the clustering procedure of the invention carried distinct patterns of genomic aberrations, implying different origins and tumorigenic mechanisms. This observation suggests that the different subgroups will manifest distinct clinical behaviors and sensitivities to therapeutic interventions, characteristic of each subgroup. Such has been observed previously with other copy number aberrations, such as, for example, HER2 amplification in breast cancer, EGFR amplification in lung cancer, and MYCN amplification in neuroblastoma. (see for example (Anand et al., 2003; Hirsch et al., 2006; Seeger et al., 1985; Vogel et al., 2002).

The methods of the present invention, made possible by a novel computational algorithm, are based on the analysis of complex genome-wide patterns of copy number alterations. The methods of the invention provide for complete characterization of genomic subtypes of NSCLC and generate more precise correlates of clinical behavior and therapeutic interventions.

The proposed genomic taxonomy is valid for the entire population of NSCLC subjects because (i) the sample set was sufficiently large (~300 samples), and (ii) the samples were acquired from a variety of sources, thus eliminating the possibility of bias.

In one aspect, then, the invention provides methods to profile NSCLC samples using high-resolution comparative genomic hybridization (CGH) and methods to classify the copy number profiles using custom statistical algorithms. The resulting classification of NSCLCs can be used to predict response of patients to drugs and select pre-clinical models.

The methods of the invention permit classification of NSCLC based on patterns of genomic abnormalities, thus determining molecular subgroups of the disease.

In another aspect, the present invention exploits a unique computational algorithm that can be used to define or classify genomic subgroups of NSCLC cells. Generally, the computational algorithm comprises the following steps:

1. Applying a machine learning algorithm (such as Random Forests) to identify and eliminate samples with significant contamination by normal cells;

2. Using unsupervised clustering (such as hierarchical clustering) to estimate the possible numbers of clusters before fitting the data with a genomic Non-negative Matrix Factorization (gNMF) model;

3. Using multiple random starts of gNMF followed by the application of the correlation of H matrix resulting from gNMF as the distance matrix to classify samples;

4. Classifying tumors and cancer cell lines into several possible numbers of clusters using the gNMF algorithm, followed by the use of the Cophenetic correlation coefficient and Bayesian Information Criterion (BIC) to select the best model and determine the final number of clusters; and 5. Optionally, applying a 10-fold stability test to evaluate the stability of the clusters.

In one embodiment, the invention classifies NSCLC cells, comprising the steps of (1) extracting genomic DNA (gDNA) from NSCLC cell samples; (2) hybridizing the gDNA to microarrays, and analyzing the microarrays to acquire the raw signal for each probe spotted on the microarray; (3) determining the copy number of each locus and detecting copy number alteration regions; (4) performing data quality control; (5) smoothing copy number data and reducing dimensionality using a segmentation algorithm; (6) classifying the smoothed data using gNMF with an estimated number of clusters estimated by hierarchical clustering; (7) selecting the best classification model using Cophenetic correlation and/or Bayesian Information Criterion; and (8) optionally, testing the stability of the gNMF classification.

The methods of the present invention facilitate rational selection of preclinical testing models and improve the predictability of preclinical testing by providing a more complete representation of parent tumors in the panels of preclinical testing models. While not wishing to be bound by any theory, the fundamental principle of the present invention is as follows. Patterns of copy number alterations (CNAs) have been shown to determine the phenotypes of human tumors. Thus, if subgroups of tumor populations are defined by patterns of CNAs and then at least one cell line is selected to match each subgroup, a panel of cell lines can be developed that represents the diversity of the NSCLC cell population more adequately than the presently available sets of models. These panels of cell lines can be used to test therapeutic interventions. Furthermore, these databases allow for patient NSCLC tumors to be classified more finely, allowing for refined prescription of therapeutic interventions that have a higher probability of effectively treating the cancer.

The methods of the present invention facilitate rational selection of therapeutic interventions and preclinical testing models.

Definitions

A genome-wide copy number profile, or "copy number," is a measurement of DNA copy number of more than one genetic locus. A copy number profile can assess if a cell is essentially wild-type, wherein each genetic locus is present in two copies (because of diploidy, except for sex chromosomes), or deviant from wild-type, i.e., containing amplifications and deletions of genetic loci. Amplifications and deletions can affect a part of an element, and entire element, or many elements simultaneously. A copy number profile does not necessarily determine the exact number of amplifications or deletions, but identifies those regions that contain the genetic abnormalities, and whether the abnormality is a deletion or amplification.

In some embodiments, a "wild-type" genome, when used in context of the genotype determination of a sample, does not necessarily mean the wild-type sample is strictly diploid. In the context of the present invention, a "wild-type" genome is one that is taken from a cell that does not express, or is not about to express, a particular disease state, such as NSCLC. For example, a wild-type genome can be provided by a subject from healthy, normal cells, and compared to the same subject's NSCLC cells.

"Bayesian Information Criterion" or "BIC" refers to a parametric method which is used as a statistical criterion for model selection. BIC was described by Schwarz, G. in "Estimating the dimension of a model", in the *Annals of Statistics* 6(2):461-464 (1978). BIC is defined by formula (1):

$$BIC = -2 * \ln L + k \ln(n) \tag{1}$$

wherein L is the likelihood which measures how good the model approximates the data, k is the number of parameters used in the model, and n is the number of samples. The second term, $k*\ln(n)$, serves as a penalty on the number of parameters used in the model to avoid over-fitting.

"Cophenetic correlation coefficient" or "Cophenetic correlation," used interchangeably, refers to algorithms that are used to measure how faithfully a dendrogram used to derive the final clustering result preserves the pair-wise distances between the original un-modeled data points. For use in the present invention, if it is supposed that the original data X, has been modeled by a dendrogram T, distance measures are defined by formula (2):

$$x(i,j) = |X_i - X_j| \tag{2}$$

the distance between the $i^{th}$ and $j^{th}$ samples, and t(i,j)=the dendrogrammatic distance between the model points Ti and Tj where the distance is the height of the node at which these two points are first joined together.

Then, if x is the average of x(i,j), and t is the average t(i,j), the Cophenetic correlation coefficient c is defined by formula (3):

$$c = \frac{\sum_{i<j}(x(i,j)-x)(t(i,j)-t)}{\sqrt{\left[\sum_{i<j}(x(i,j)-x)^2\right]\left[\sum_{i<j}(t(i,j)-t)^2\right]}} \tag{3}$$

As r increases, the Cophenetic correlation will decrease dramatically at a certain point, thus corresponding to the best number of clusters (Carrasco et al., 2006; Maher et al., 2006).

"Cluster analysis," also known as "data segmentation," refers to the grouping or segmenting a collection of objects (also called observations, individuals, cases, or data rows) into subsets, subgroups or "clusters", such that those within each cluster are more closely related to one another than objects assigned to different clusters. Central to all of the goals of cluster analysis is the notion of degree of similarity (or dissimilarity) between the individual objects being clustered. Examples of types of clustering are hierarchical clustering and k-means clustering.

"Hierarchical clustering" refers to the building (agglomerative), or break up (divisive), of a hierarchy of clusters. The traditional representation of this hierarchy is a dendrogram, with individual elements at one end and a single cluster containing every element at the other. Agglomerative algorithms begin at the leaves of the tree, whereas divisive algorithms begin at the root. Methods for performing hierarchical clustering are well known in the art.

Hierarchical clustering methods have been widely used to cluster biological samples based on their gene expression patterns and derive subgroup structures in populations of samples in biomedical research (Bhattacharjee et al., 2001; Hedenfalk et al., 2003; Sotiriou et al., 2003; Wilhelm et al., 2002). For example, hierarchical clustering has been used to group 64 human tumor cell lines into several clusters based on the expression pattern of 1161 selected genes, and derive the molecular signatures of different clusters (Ross et al., 2000).

"Machine learning" refers to a subfield of artificial intelligence that relates to the design and development of algorithms and techniques that allows computers to "learn". In general, there are two types of learning: inductive, and deductive. Inductive machine learning methods extract rules and patterns out of data sets. The major focus of machine learning research is to extract information from data automatically, by computational and statistical methods. A number of machine learning algorithms, which are organized into taxonomies, based on the desired outcome of the algorithm, are known to those skilled in the art. These include (1) supervised learning (e.g., Random Forests); (2) unsupervised learning (e.g., principal components analysis, vector quantization, etc.); (3) semi-supervised learning; (4) reinforcement learning; (5) transduction; and (6) learning to learn.

"Non-negative Matrix Factorization" (NMF) refers to an algorithm for finding parts-based, linear representations of non-negative data. Non-negative Matrix Factorization was originally developed as a mathematical tool for use in image analysis (Lee and Seung, 1999; Lee and Seung, 2001). NMF was adopted in genomics for analysis of gene expression data (Brunet et al., 2004). Specifically, NMF was adapted for use in the analysis of gene copy number data, the variation of the method used for gene copy number analysis is referred to as genomic Non-negative Matrix Factorization (gNMF) (Carrasco et al., 2006; Maher et al., 2006). Given a n×m matrix V of smoothed copy number data for a set of samples, where n is the number of segments and m is the number of samples, the gNMF algorithm factorizes the matrix V into an n×r matrix W and a r×m matrix H as shown in formula (4):

$$V = W*H + e \quad (4)$$

wherein W can be viewed as the standard model for each subgroup; H as relative weights of each sample belonging to each subgroup; e represents the model fitting residues, and r is the number of subgroups to be clustered (which is usually much smaller than m). Given r and V as input, the gNMF algorithm first randomly sets the initial value of W and H, and then iteratively updates W and H using multiplicative update rules pursuant to formulas (5) and (6):

$$H_{a\mu} \leftarrow H_{a\mu} \frac{\sum_i W_{ia} V_{i\mu}/(WH)_{i\mu}}{\sum_k W_{ka}} \quad (5)$$

$$W_{ia} \leftarrow W_{ia} \frac{\sum_\mu H_{a\mu} V_{i\mu}/(WH)_{i\mu}}{\sum_v H_{av}} \quad (6)$$

wherein a runs from 1 to r, μ runs from 1 to m, and i runs from 1 to n.

"Pearson linear dissimilarity" refers to formula (7):

$$d_\rho(\vec{x}, \vec{y}) = \frac{1 - \rho(\vec{x}, \vec{y})}{2} \quad (7)$$

wherein $\vec{x}$ and $\vec{y}$ are two vectors with length n, $\rho(\vec{x}, \vec{y})$ is the Pearson's linear correlation which has the formula (8):

$$\rho(\vec{x}, \vec{y}) = \frac{1}{n-1} \sum_{i=1}^{n} \left(\frac{x_i - \bar{x}}{s_x}\right)\left(\frac{y_i - \bar{y}}{s_y}\right) \quad (8)$$

wherein the sample standard deviation $s_x$, and $s_y$ have formula (9):

$$s_x = \sqrt{\frac{\sum_{i=1}^{n}(x_i - \bar{x})^2}{n-1}} \quad (9)$$

and wherein the sample mean has formula (10):

$$\bar{x} = \frac{1}{n} \sum_{i=1}^{n} x_i. \quad (10)$$

"Random forests" refers to a supervised learning algorithm that uses a combination of tree predictors such that each tree depends on the values of a random vector sampled independently and with the same distribution for all trees in the forest (Breiman, 2001).

Random Forests grow many classification trees. To classify a new object from an input vector, put the input vector down each of the trees in the forest. Each tree gives a classification, and it is said that the tree "votes" for that class. The forest chooses the classification having the most votes (over all the trees in the forest). Each tree is grown as follows:

1. If the number of cases in the training set is N, sample N cases at random—but with replacement, from the original data. This sample will be the training set for growing the tree.

2. If there are m input variables, a number m<<M is specified such that at each node, m variables are selected at random out of the M and the best split on these m variables are used to split the node. The value of m is held constant during the forest growing.

3. Each tree is grown to the largest extent possible. There is no pruning.

The forest error rate depends on two factors:
1. The correlation between any two trees in the forest. Increasing the correlation increases the forest error rate.
2. The strength of each individual tree in the forest. A tree with a low error rate is a strong classifier. Increasing the strength of the individual trees decreases the forest error rate.

An oligonucleotide or polynucleotide is a nucleic acid ranging from at least 2, preferable at least 8, and more preferably at least 20 nucleotides in length or a compound that specifically hybridizes to a polynucleotide. Polynucleotides include deoxyribonucleic acid (DNA) or ribonucleic acid (RNA). A further example of a polynucleotide is peptide nucleic acid (PNA).

A probe is a surface-immobilized molecule that can be recognized by a particular target.

Solid support, support, and substrate are used interchangeably and refer to a material or group of materials having a rigid or semi-rigid surface or surfaces.

"Hybridization" refers to the formation of complexes between nucleic acid sequences, which are sufficiently complementary to form complexes via Watson-Crick base pairing or non-canonical base pairing. For example, when a primer "hybridizes" with a target sequence (template), such complexes (or hybrids) are sufficiently stable to serve the priming function required by, e.g., the DNA polymerase, to initiate DNA synthesis. Hybridizing sequences need not have perfect complementarity to provide stable hybrids. In many situations, stable hybrids form where fewer than about 10% of the bases are mismatches. As used herein, the term "complementary" refers to an oligonucleotide that forms a stable duplex with its complement under assay conditions, generally where there is about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater homology. Those skilled in the art understand how to estimate and adjust the stringency of hybridization conditions such that sequences having at least a desired level of complementarity stably hybridize, while those having lower complementarity will not. Examples of hybridization conditions and parameters are well-known (Ausubel, 1987; Sambrook and Russell, 2001).

A nucleic acid array ("array") comprises nucleic acid probes attached to a solid support. Arrays typically comprise a plurality of different nucleic acid probes that are coupled to a surface of a substrate in different, known locations. These arrays, also described as microarrays, "chips" have been generally described in the art, for example, U.S. Pat. Nos. 5,143,854, 5,445,934, 5,744,305, 5,677,195, 6,040,193, 5,424,186 and (Fodor et al., 1991). These arrays can generally be produced using mechanical synthesis methods or light directed synthesis methods that incorporate a combination of photolithographic methods and solid phase synthesis methods. Techniques for the synthesis of arrays using mechanical synthesis are described in, e.g., U.S. Pat. No. 5,384,261. Although a planar array surface is preferred, the array can be fabricated on a surface of virtually any shape or even a multiplicity of surfaces. Arrays can be nucleic acids on beads, gels, polymeric surfaces, fibers such as fiber optics, glass or any other appropriate substrate; e.g., as described in U.S. Pat. Nos. 5,770,358, 5,789,162, 5,708,153, 6,040,193 and 5,800,992. Arrays can be packaged in such a manner as to allow for diagnostics or other manipulation of an all inclusive device, see for example, U.S. Pat. Nos. 5,856,174 and 5,922,591.

Arrays can be designed to cover an entire genome using single nucleotide polymorphisms (SNPs). For example, an array can cover 116,204 single-nucleotide polymorphism (SNP) loci in the human genome with a mean inter-marker distance of 23.6 kb SNP loci with a mean inter-marker distance of 23.6 kb loci.

"Labeled" and "labeled with a detectable label (or agent or moiety)" are used interchangeably and specify that an entity (e.g., a fragment of DNA, a primer or a probe) can be visualized, for example following binding to another entity (e.g., an amplification product). The detectable label can be selected such that the label generates a signal that can be measured and which intensity is related to (e.g., proportional to) the amount of bound entity. A wide variety of systems for labeling and/or detecting nucleic acid molecules, such as primer and probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable agents include radionuclides, fluorophores, chemiluminescent agents, microparticles, enzymes, colorimetric labels, magnetic labels, haptens and the like.

"Probe" refers to an oligonucleotide designed for use in connection with a CGH microarray, a SNPs microarray or any other microarrays known in the art that are capable of selectively hybridizing to at least a portion of a target sequence under appropriate conditions. In general, a probe sequence is identified as being either "complementary" (i.e., complementary to the coding or sense strand (+)), or "reverse complementary" (i.e., complementary to the anti-sense strand (−)). Probes can have a length of about 10-100 nucleotides, preferably about 15-75 nucleotides, most preferably from about 15-50 nucleotides.

"Pharmaceutical composition" or "drug," used interchangeably, refers to any agent, whether a small molecule (e.g., a drug containing an active agent, typically a non-peptidic) or biologic (e.g., a peptide, protein or antibody based drug, including any with modifications, such as PEGylation) that can be used to treat a subject or patient suffering from at least one type of cancer.

A "cell" can come from a tumor, cell line, or a subject.

A "therapy" or "therapeutic regimen" refers to a course of treatment intended to reduce or eliminate the affects or symptoms of a disease or to prevent progression of a disease from one state to a second more detrimental state. A therapeutic regimen can comprise a prescribed drug, surgery or radiation treatment. The copy number profile of a subject's tumor can also impact side effects and efficacy of a selected therapy. In the present invention, the copy number profile of a subject's tumor can be used to determine a therapy or therapeutic regimen that is likely to be most effective.

"Subject" or "patient" encompasses mammals and non-mammals. Examples of mammals include: humans, other primates, such as chimpanzees, and other apes and monkey species; farm animals such as cattle, horses, sheep, goats, swine; domestic animals such as rabbits, dogs, and cats; laboratory animals including rodents, such as rats, mice and guinea pigs. Examples of non-mammals include birds and fish.

"Treat," "treating" and "treatment," mean alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Practicing the Invention

In the methods of the invention, a reference database of copy number profiles is created, wherein the genomic copy number in a plurality (m) of samples comprising NSCLC cells is determined (where m is an integer from 1 to 5,000,000. For example, a plurality of samples can be two (2), five (5), ten (10), fifteen (15), twenty (20), twenty-five (25), fifty (50), one hundred (100), two hundred (200), five hundred (500) one thousand (1,000), ten thousand (10,000), fifty thousand (50,000), one hundred thousand samples (100,000), two hundred and fifty thousand samples (250,000), five hundred thousand (500,000), one million (1,000,000) samples, etc.). The NSCLC cells are then classified into genomic subgroups according to the patterns of copy number, the copy number profile. Each one of these subgroups represents not only a classification based on genotype, but is expected to show characteristic responsiveness to various therapeutic interventions. For example, one subgroup may be more susceptible to radiation, while another is more susceptible to pharmaceutical interventions, such as chemotherapy.

Copy number alterations are detected in NSCLC cells that can be obtained from subjects suffering from, or at risk for suffering from, NSCLC. Such cells can be obtained using routine techniques. For example, tumors can be surgically dissected from a subject suffering or suspected of suffering from cancer and them immediately frozen, such as at −80° C.

For developing a database of different subgroups that allow for the classification of a subject, NSCLC tumors and cancer cell lines can be obtained commercially or from public sources. A useful set of cell lines is shown in Table 1. Table 1 also lists those tumor samples used in the Examples (see below). In the table, ATTC, American Type Culture Collection (Manassus, Va.); DSMZ, Deutsche Sammlung von Mikroorganismen und Zellkulturen GmbH (Braunschweig, Germany); CLS, Cell Line Service (Germany).

Additional copy number and copy number alteration information from NSCLC cells and cancer cell lines can be obtained from a number of commercially or publically available sources, such as from the Gene Expression Omnibus (GEO), which is available from the National Center for Biotechnology Information (NCBI), Broad Institute/Dana Farber Cancer Institute Internet Portal, on-line from the Dana Farber Cancer Institute web site, etc.

TABLE 1

Cell lines, tumor samples and sources

| Cell line | Source | Catalog number (ATCC, DSMZ and CLS only) |
|---|---|---|
| CLS-54 | CLS | CLS-54 |
| LX-289 | CLS | LX-289 |
| SK-LU-1 | ATCC, CLS | HTB-57 (ATCC); SK-LU-1 (CLS) |
| SK-MES-1 | ATCC, DSMZ, CLS | HTB-58 (ATCC); ACC 353 (DSMZ); SK-MES-1 (CLS) |
| H157 | (Zhao et al., 2005) | |
| H1819 | (Zhao et al., 2005) | CRL-5897 |
| H2009 | (Zhao et al., 2005) | CRL-5911 |
| H2882 | (Zhao et al., 2005) | |
| H2887 | (Zhao et al., 2005) | |
| HCC1171 | (Zhao et al., 2005) | |
| HCC1359 | (Zhao et al., 2005) | |
| HCC15 | (Zhao et al., 2005) | |
| HCC193 | (Zhao et al., 2005) | |
| HCC366 | (Zhao et al., 2005) | |
| HCC461 | (Zhao et al., 2005) | |
| HCC515 | (Zhao et al., 2005) | |
| HCC78 | (Zhao et al., 2005) | |
| HCC95 | (Zhao et al., 2005) | |
| HOP-62 | (Zhao et al., 2005) | |
| HOP-92 | (Zhao et al., 2005) | |
| NCI-H266 | (Zhao et al., 2005) | |
| NCI-H1437 | ATCC | CRL-5872 |
| NCI-H1563 | ATCC | CRL-5875 |
| NCI-H1568 | ATCC | CRL-5876 |
| NCI-H1623 | ATCC | CRL-5881 |
| NCI-H1651 | ATCC | CRL-5884 |
| NCI-H1693 | ATCC | CRL-5887 |
| NCI-H1734 | ATCC | CRL-5891 |
| NCI-H1755 | ATCC | CRL-5892 |
| NCI-H1793 | ATCC | CRL-5896 |
| NCI-H1838 | ATCC | CRL-5899 |
| NCI-H1944 | ATCC | CRL-5907 |
| NCI-H1975 | ATCC | CRL-5908 |
| NCI-H1993 | ATCC | CRL-5909 |
| NCI-H2023 | ATCC | CRL-5912 |
| NCI-H2073 | ATCC | CRL-5918 |
| NCI-H2085 | ATCC | CRL-5921 |
| NCI-H2087 | ATCC | CRL-5922 |
| NCI-H2122 | ATCC | CRL-5985 |
| NCI-H2126 | ATCC | CCL-256 |
| NCI-H2228 | ATCC | CRL-5935 |
| NCI-H2291 | ATCC | CRL-5939 |
| NCI-H23 | ATCC | CRL-5800 |
| NCI-H2342 | ATCC | CRL-5941 |
| NCI-H2347 | ATCC | CRL-5942 |
| NCI-H2405 | ATCC | CRL-5944 |
| NCI-H522 | ATCC | CRL-5810 |

TABLE 1-continued

Cell lines, tumor samples and sources

| Cell line | Source | Catalog number (ATCC, DSMZ and CLS only) |
|---|---|---|
| NCI-H647 | ATCC | CRL-5834 |
| NCI-H838 | ATCC | CRL-5844 |
| NCI-H920 | ATCC | CRL-5850 |
| NCI-H969 | ATCC | CRL-5852 |
| A549 | ATCC | CCL-185 |
| Calu-3 | ATCC | HTB-55 |
| HCC827 | ATCC | CRL-2868 |
| Calu-6 | ATCC | HTB-56 |
| H358 | ATCC | CRL-5807 |
| H460 | ATCC | HTB-177 |
| NSCLC21 | Caprion Proteomics, Montreal, Quebec | n/a |
| NSCLC22 | Caprion Proteomics, Montreal, Quebec | n/a |
| NSCLC23 | Caprion Proteomics, Montreal, Quebec | n/a |
| NSCLC24 | Caprion Proteomics, Montreal, Quebec | n/a |
| NSCLC25 | Caprion Proteomics, Montreal, Quebec | n/a |
| NSCLC26 | Caprion Proteomics, Montreal, Quebec | n/a |
| NSCLC27 | Caprion Proteomics, Montreal, Quebec | n/a |
| NSCLC28 | Caprion Proteomics, Montreal, Quebec | n/a |
| NSCLC29 | Caprion Proteomics, Montreal, Quebec | n/a |
| NSCLC30 | Caprion Proteomics, Montreal, Quebec | n/a |
| NSCLC31 | Caprion Proteomics, Montreal, Quebec | n/a |
| NSCLC33 | Caprion Proteomics, Montreal, Quebec | n/a |
| NSCLC34 | Caprion Proteomics, Montreal, Quebec | n/a |
| NSCLC35 | Caprion Proteomics, Montreal, Quebec | n/a |
| NSCLC36 | Caprion Proteomics, Montreal, Quebec | n/a |
| NSCLC37 | Caprion Proteomics, Montreal, Quebec | n/a |
| NSCLC38 | Caprion Proteomics, Montreal, Quebec | n/a |
| NSCLC41 | Caprion Proteomics, Montreal, Quebec | n/a |
| NSCLC42 | Caprion Proteomics, Montreal, Quebec | n/a |
| NSCLC43 | Caprion Proteomics, Montreal, Quebec | n/a |
| NSCLC44 | Caprion Proteomics, Montreal, Quebec | n/a |
| NSCLC45 | Caprion Proteomics, Montreal, Quebec | n/a |
| NSCLC46 | Caprion Proteomics, Montreal, Quebec | n/a |
| NSCLC47 | Caprion Proteomics, Montreal, Quebec | n/a |
| NSCLC49 | Caprion Proteomics, Montreal, Quebec | n/a |
| NSCLC50 | Caprion Proteomics, Montreal, Quebec | n/a |
| NSCLC52 | Caprion Proteomics, Montreal, Quebec | n/a |
| NSCLC53 | Caprion Proteomics, Montreal, Quebec | n/a |
| NSCLC55 | Caprion Proteomics, Montreal, Quebec | n/a |
| NSCLC58 | Caprion Proteomics, Montreal, Quebec | n/a |
| NSCLC60 | Caprion Proteomics, Montreal, Quebec | n/a |
| NSCLC65 | Caprion Proteomics, Montreal, Quebec | n/a |
| NSCLC66 | Caprion Proteomics, Montreal, Quebec | n/a |
| NSCLC67 | Caprion Proteomics, Montreal, Quebec | n/a |
| NSCLC69 | Caprion Proteomics, Montreal, Quebec | n/a |
| NSCLC70 | Caprion Proteomics, Montreal, Quebec | n/a |
| NSCLC71 | Caprion Proteomics, Montreal, Quebec | n/a |
| NSCLC72 | Caprion Proteomics, Montreal, Quebec | n/a |
| NSCLC75 | Caprion Proteomics, Montreal, Quebec | n/a |
| NSCLC76 | Caprion Proteomics, Montreal, Quebec | n/a |
| NSCLC79 | Caprion Proteomics, Montreal, Quebec | n/a |
| NSCLC82 | Caprion Proteomics, Montreal, Quebec | n/a |
| NSCLC85 | Caprion Proteomics, Montreal, Quebec | n/a |
| NSCLC299 | Data obtained from the Dana-Farber Cancer Institute | n/a |
| NSCLC300 | Data obtained from the Dana-Farber Cancer Institute | n/a |
| NSCLC301 | Data obtained from the Dana-Farber Cancer Institute | n/a |
| NSCLC303 | Data obtained from the Dana-Farber Cancer Institute | n/a |
| NSCLC305 | Data obtained from the Dana-Farber Cancer Institute | n/a |
| NSCLC307 | Data obtained from the Dana-Farber Cancer Institute | n/a |
| NSCLC308 | Data obtained from the Dana-Farber Cancer Institute | n/a |
| NSCLC309 | Data obtained from the Dana-Farber Cancer Institute | n/a |
| NSCLC311 | Data obtained from the Dana-Farber Cancer Institute | n/a |
| NSCLC312 | Data obtained from the Dana-Farber Cancer Institute | n/a |
| NSCLC314 | Data obtained from the Dana-Farber Cancer Institute | n/a |
| NSCLC315 | Data obtained from the Dana-Farber Cancer Institute | n/a |
| NSCLC316 | Data obtained from the Dana-Farber Cancer Institute | n/a |
| NSCLC317 | Data obtained from the Dana-Farber Cancer Institute | n/a |
| NSCLC318 | Data obtained from the Dana-Farber Cancer Institute | n/a |
| NSCLC319 | Data obtained from the Dana-Farber Cancer Institute | n/a |
| NSCLC320 | Data obtained from the Dana-Farber Cancer Institute | n/a |
| NSCLC322 | Data obtained from the Dana-Farber Cancer Institute | n/a |
| NSCLC323 | Data obtained from the Dana-Farber Cancer Institute | n/a |
| NSCLC325 | Data obtained from the Dana-Farber Cancer Institute | n/a |
| NSCLC327 | Data obtained from the Dana-Farber Cancer Institute | n/a |
| NSCLC328 | Data obtained from the Dana-Farber Cancer Institute | n/a |

TABLE 1-continued

Cell lines, tumor samples and sources

| Cell line | Source | Catalog number (ATCC, DSMZ and CLS only) |
|---|---|---|
| NSCLC330 | Data obtained from the Dana-Farber Cancer Institute | n/a |
| NSCLC332 | Data obtained from the Dana-Farber Cancer Institute | n/a |
| NSCLC333 | Data obtained from the Dana-Farber Cancer Institute | n/a |
| NSCLC334 | Data obtained from the Dana-Farber Cancer Institute | n/a |
| NSCLC335 | Data obtained from the Dana-Farber Cancer Institute | n/a |
| NSCLC336 | Data obtained from the Dana-Farber Cancer Institute | n/a |
| NSCLC337 | Data obtained from the Dana-Farber Cancer Institute | n/a |
| NSCLC338 | Data obtained from the Dana-Farber Cancer Institute | n/a |
| NSCLC339 | Data obtained from the Dana-Farber Cancer Institute | n/a |
| NSCLC340 | Data obtained from the Dana-Farber Cancer Institute | n/a |
| NSCLC341 | Data obtained from the Dana-Farber Cancer Institute | n/a |
| NSCLC342 | Data obtained from the Dana-Farber Cancer Institute | n/a |
| NSCLC344 | Data obtained from the Dana-Farber Cancer Institute | n/a |
| NSCLC345 | Data obtained from the Dana-Farber Cancer Institute | n/a |
| NSCLC346 | Data obtained from the Dana-Farber Cancer Institute | n/a |
| NSCLC347 | Data obtained from the Dana-Farber Cancer Institute | n/a |
| NSCLC1 | ProteoGenex, Culver City, CA | n/a |
| NSCLC10 | ProteoGenex, Culver City, CA | n/a |
| NSCLC11 | ProteoGenex, Culver City, CA | n/a |
| NSCLC12 | ProteoGenex, Culver City, CA | n/a |
| NSCLC13 | ProteoGenex, Culver City, CA | n/a |
| NSCLC14 | ProteoGenex, Culver City, CA | n/a |
| NSCLC15 | ProteoGenex, Culver City, CA | n/a |
| NSCLC17 | ProteoGenex, Culver City, CA | n/a |
| NSCLC18 | ProteoGenex, Culver City, CA | n/a |
| NSCLC19 | ProteoGenex, Culver City, CA | n/a |
| NSCLC2 | ProteoGenex, Culver City, CA | n/a |
| NSCLC20 | ProteoGenex, Culver City, CA | n/a |
| NSCLC4 | ProteoGenex, Culver City, CA | n/a |
| NSCLC5 | ProteoGenex, Culver City, CA | n/a |
| NSCLC7 | ProteoGenex, Culver City, CA | n/a |
| NSCLC8 | ProteoGenex, Culver City, CA | n/a |
| NSCLC9 | ProteoGenex, Culver City, CA | n/a |
| NSCLC100 | Rush Presbyterian, Chicago, IL (Dr. Coon) | n/a |
| NSCLC101 | Rush Presbyterian, Chicago, IL (Dr. Coon) | n/a |
| NSCLC103 | Rush Presbyterian, Chicago, IL (Dr. Coon) | n/a |
| NSCLC104 | Rush Presbyterian, Chicago, IL (Dr. Coon) | n/a |
| NSCLC105 | Rush Presbyterian, Chicago, IL (Dr. Coon) | n/a |
| NSCLC106 | Rush Presbyterian, Chicago, IL (Dr. Coon) | n/a |
| NSCLC108 | Rush Presbyterian, Chicago, IL (Dr. Coon) | n/a |
| NSCLC109 | Rush Presbyterian, Chicago, IL (Dr. Coon) | n/a |
| NSCLC110 | Rush Presbyterian, Chicago, IL (Dr. Coon) | n/a |
| NSCLC111 | Rush Presbyterian, Chicago, IL (Dr. Coon) | n/a |
| NSCLC113 | Rush Presbyterian, Chicago, IL (Dr. Coon) | n/a |
| NSCLC115 | Rush Presbyterian, Chicago, IL (Dr. Coon) | n/a |
| NSCLC116 | Rush Presbyterian, Chicago, IL (Dr. Coon) | n/a |
| NSCLC117 | Rush Presbyterian, Chicago, IL (Dr. Coon) | n/a |
| NSCLC118 | Rush Presbyterian, Chicago, IL (Dr. Coon) | n/a |
| NSCLC119 | Rush Presbyterian, Chicago, IL (Dr. Coon) | n/a |
| NSCLC120 | Rush Presbyterian, Chicago, IL (Dr. Coon) | n/a |
| NSCLC121 | Rush Presbyterian, Chicago, IL (Dr. Coon) | n/a |
| NSCLC122 | Rush Presbyterian, Chicago, IL (Dr. Coon) | n/a |
| NSCLC123 | Rush Presbyterian, Chicago, IL (Dr. Coon) | n/a |
| NSCLC125 | Rush Presbyterian, Chicago, IL (Dr. Coon) | n/a |
| NSCLC126 | Rush Presbyterian, Chicago, IL (Dr. Coon) | n/a |
| NSCLC127 | Rush Presbyterian, Chicago, IL (Dr. Coon) | n/a |
| NSCLC128 | Rush Presbyterian, Chicago, IL (Dr. Coon) | n/a |
| NSCLC129 | Rush Presbyterian, Chicago, IL (Dr. Coon) | n/a |
| NSCLC130 | Rush Presbyterian, Chicago, IL (Dr. Coon) | n/a |
| NSCLC132 | Rush Presbyterian, Chicago, IL (Dr. Coon) | n/a |
| NSCLC133 | Rush Presbyterian, Chicago, IL (Dr. Coon) | n/a |
| NSCLC134 | Rush Presbyterian, Chicago, IL (Dr. Coon) | n/a |
| NSCLC135 | Rush Presbyterian, Chicago, IL (Dr. Coon) | n/a |
| NSCLC136 | Rush Presbyterian, Chicago, IL (Dr. Coon) | n/a |
| NSCLC137 | Rush Presbyterian, Chicago, IL (Dr. Coon) | n/a |
| NSCLC138 | Rush Presbyterian, Chicago, IL (Dr. Coon) | n/a |
| NSCLC139 | Rush Presbyterian, Chicago, IL (Dr. Coon) | n/a |
| NSCLC143 | Rush Presbyterian, Chicago, IL (Dr. Coon) | n/a |
| NSCLC144 | Rush Presbyterian, Chicago, IL (Dr. Coon) | n/a |
| NSCLC145 | Rush Presbyterian, Chicago, IL (Dr. Coon) | n/a |
| NSCLC146 | Rush Presbyterian, Chicago, IL (Dr. Coon) | n/a |
| NSCLC150 | Rush Presbyterian, Chicago, IL (Dr. Coon) | n/a |
| NSCLC151 | Rush Presbyterian, Chicago, IL (Dr. Coon) | n/a |
| NSCLC153 | Rush Presbyterian, Chicago, IL (Dr. Coon) | n/a |
| NSCLC155 | Rush Presbyterian, Chicago, IL (Dr. Coon) | n/a |

TABLE 1-continued

Cell lines, tumor samples and sources

| Cell line | Source | Catalog number (ATCC, DSMZ and CLS only) |
|---|---|---|
| NSCLC156 | Rush Presbyterian, Chicago, IL (Dr. Coon) | n/a |
| NSCLC157 | Rush Presbyterian, Chicago, IL (Dr. Coon) | n/a |
| NSCLC158 | Rush Presbyterian, Chicago, IL (Dr. Coon) | n/a |
| NSCLC159 | Rush Presbyterian, Chicago, IL (Dr. Coon) | n/a |
| NSCLC160 | Rush Presbyterian, Chicago, IL (Dr. Coon) | n/a |
| NSCLC162 | Rush Presbyterian, Chicago, IL (Dr. Coon) | n/a |
| NSCLC164 | Rush Presbyterian, Chicago, IL (Dr. Coon) | n/a |
| NSCLC165 | Rush Presbyterian, Chicago, IL (Dr. Coon) | n/a |
| NSCLC166 | Rush Presbyterian, Chicago, IL (Dr. Coon) | n/a |
| NSCLC167 | Rush Presbyterian, Chicago, IL (Dr. Coon) | n/a |
| NSCLC168 | Rush Presbyterian, Chicago, IL (Dr. Coon) | n/a |
| NSCLC171 | Rush Presbyterian, Chicago, IL (Dr. Coon) | n/a |
| NSCLC172 | Rush Presbyterian, Chicago, IL (Dr. Coon) | n/a |
| NSCLC173 | Rush Presbyterian, Chicago, IL (Dr. Coon) | n/a |
| NSCLC174 | Rush Presbyterian, Chicago, IL (Dr. Coon) | n/a |
| NSCLC175 | Rush Presbyterian, Chicago, IL (Dr. Coon) | n/a |
| NSCLC176 | Rush Presbyterian, Chicago, IL (Dr. Coon) | n/a |
| NSCLC177 | Rush Presbyterian, Chicago, IL (Dr. Coon) | n/a |
| NSCLC178 | Rush Presbyterian, Chicago, IL (Dr. Coon) | n/a |
| NSCLC179 | Rush Presbyterian, Chicago, IL (Dr. Coon) | n/a |
| NSCLC180 | Rush Presbyterian, Chicago, IL (Dr. Coon) | n/a |
| NSCLC1h81 | Rush Presbyterian, Chicago, IL (Dr. Coon) | n/a |
| NSCLC182 | Rush Presbyterian, Chicago, IL (Dr. Coon) | n/a |
| NSCLC184 | Rush Presbyterian, Chicago, IL (Dr. Coon) | n/a |
| NSCLC185 | Rush Presbyterian, Chicago, IL (Dr. Coon) | n/a |
| NSCLC187 | Rush Presbyterian, Chicago, IL (Dr. Coon) | n/a |
| NSCLC188 | Rush Presbyterian, Chicago, IL (Dr. Coon) | n/a |
| NSCLC189 | Rush Presbyterian, Chicago, IL (Dr. Coon) | n/a |
| NSCLC191 | Rush Presbyterian, Chicago, IL (Dr. Coon) | n/a |
| NSCLC192 | Rush Presbyterian, Chicago, IL (Dr. Coon) | n/a |
| NSCLC194 | Rush Presbyterian, Chicago, IL (Dr. Coon) | n/a |
| NSCLC195 | Rush Presbyterian, Chicago, IL (Dr. Coon) | n/a |
| NSCLC196 | Rush Presbyterian, Chicago, IL (Dr. Coon) | n/a |
| NSCLC198 | Rush Presbyterian, Chicago, IL (Dr. Coon) | n/a |
| NSCLC199 | Rush Presbyterian, Chicago, IL (Dr. Coon) | n/a |
| NSCLC201 | Rush Presbyterian, Chicago, IL (Dr. Coon) | n/a |
| NSCLC203 | Rush Presbyterian, Chicago, IL (Dr. Coon) | n/a |
| NSCLC206 | Rush Presbyterian, Chicago, IL (Dr. Coon) | n/a |
| NSCLC208 | Rush Presbyterian, Chicago, IL (Dr. Coon) | n/a |
| NSCLC209 | Rush Presbyterian, Chicago, IL (Dr. Coon) | n/a |
| NSCLC210 | Rush Presbyterian, Chicago, IL (Dr. Coon) | n/a |
| NSCLC214 | Rush Presbyterian, Chicago, IL (Dr. Coon) | n/a |
| NSCLC215 | Rush Presbyterian, Chicago, IL (Dr. Coon) | n/a |
| NSCLC216 | Rush Presbyterian, Chicago, IL (Dr. Coon) | n/a |
| NSCLC217 | Rush Presbyterian, Chicago, IL (Dr. Coon) | n/a |
| NSCLC218 | Rush Presbyterian, Chicago, IL (Dr. Coon) | n/a |
| NSCLC221 | Rush Presbyterian, Chicago, IL (Dr. Coon) | n/a |
| NSCLC222 | Rush Presbyterian, Chicago, IL (Dr. Coon) | n/a |
| NSCLC223 | Rush Presbyterian, Chicago, IL (Dr. Coon) | n/a |
| NSCLC225 | Rush Presbyterian, Chicago, IL (Dr. Coon) | n/a |
| NSCLC227 | Rush Presbyterian, Chicago, IL (Dr. Coon) | n/a |
| NSCLC228 | Rush Presbyterian, Chicago, IL (Dr. Coon) | n/a |
| NSCLC230 | Rush Presbyterian, Chicago, IL (Dr. Coon) | n/a |
| NSCLC231 | Rush Presbyterian, Chicago, IL (Dr. Coon) | n/a |
| NSCLC232 | Rush Presbyterian, Chicago, IL (Dr. Coon) | n/a |
| NSCLC233 | Rush Presbyterian, Chicago, IL (Dr. Coon) | n/a |
| NSCLC234 | Rush Presbyterian, Chicago, IL (Dr. Coon) | n/a |
| NSCLC236 | Rush Presbyterian, Chicago, IL (Dr. Coon) | n/a |
| NSCLC237 | Rush Presbyterian, Chicago, IL (Dr. Coon) | n/a |
| NSCLC238 | Rush Presbyterian, Chicago, IL (Dr. Coon) | n/a |
| NSCLC239 | Rush Presbyterian, Chicago, IL (Dr. Coon) | n/a |
| NSCLC242 | Rush Presbyterian, Chicago, IL (Dr. Coon) | n/a |
| NSCLC243 | Rush Presbyterian, Chicago, IL (Dr. Coon) | n/a |
| NSCLC246 | Rush Presbyterian, Chicago, IL (Dr. Coon) | n/a |
| NSCLC249 | Rush Presbyterian, Chicago, IL (Dr. Coon) | n/a |
| NSCLC250 | Rush Presbyterian, Chicago, IL (Dr. Coon) | n/a |
| NSCLC251 | Rush Presbyterian, Chicago, IL (Dr. Coon) | n/a |
| NSCLC252 | Rush Presbyterian, Chicago, IL (Dr. Coon) | n/a |
| NSCLC253 | Rush Presbyterian, Chicago, IL (Dr. Coon) | n/a |
| NSCLC254 | Rush Presbyterian, Chicago, IL (Dr. Coon) | n/a |
| NSCLC255 | Rush Presbyterian, Chicago, IL (Dr. Coon) | n/a |
| NSCLC256 | Rush Presbyterian, Chicago, IL (Dr. Coon) | n/a |
| NSCLC258 | Rush Presbyterian, Chicago, IL (Dr. Coon) | n/a |
| NSCLC259 | Rush Presbyterian, Chicago, IL (Dr. Coon) | n/a |
| NSCLC260 | Rush Presbyterian, Chicago, IL (Dr. Coon) | n/a |

TABLE 1-continued

Cell lines, tumor samples and sources

| Cell line | Source | Catalog number (ATCC, DSMZ and CLS only) |
| --- | --- | --- |
| NSCLC261 | Rush Presbyterian, Chicago, IL (Dr. Coon) | n/a |
| NSCLC265 | Rush Presbyterian, Chicago, IL (Dr. Coon) | n/a |
| NSCLC266 | Rush Presbyterian, Chicago, IL (Dr. Coon) | n/a |
| NSCLC269 | Rush Presbyterian, Chicago, IL (Dr. Coon) | n/a |
| NSCLC270 | Rush Presbyterian, Chicago, IL (Dr. Coon) | n/a |
| NSCLC271 | Rush Presbyterian, Chicago, IL (Dr. Coon) | n/a |
| NSCLC272 | Rush Presbyterian, Chicago, IL (Dr. Coon) | n/a |
| NSCLC273 | Rush Presbyterian, Chicago, IL (Dr. Coon) | n/a |
| NSCLC274 | Rush Presbyterian, Chicago, IL (Dr. Coon) | n/a |
| NSCLC275 | Rush Presbyterian, Chicago, IL (Dr. Coon) | n/a |
| NSCLC276 | Rush Presbyterian, Chicago, IL (Dr. Coon) | n/a |
| NSCLC277 | Rush Presbyterian, Chicago, IL (Dr. Coon) | n/a |
| NSCLC278 | Rush Presbyterian, Chicago, IL (Dr. Coon) | n/a |
| NSCLC280 | Rush Presbyterian, Chicago, IL (Dr. Coon) | n/a |
| NSCLC282 | Rush Presbyterian, Chicago, IL (Dr. Coon) | n/a |
| NSCLC283 | Rush Presbyterian, Chicago, IL (Dr. Coon) | n/a |
| NSCLC284 | Rush Presbyterian, Chicago, IL (Dr. Coon) | n/a |
| NSCLC286 | Rush Presbyterian, Chicago, IL (Dr. Coon) | n/a |
| NSCLC288 | Rush Presbyterian, Chicago, IL (Dr. Coon) | n/a |
| NSCLC290 | Rush Presbyterian, Chicago, IL (Dr. Coon) | n/a |
| NSCLC291 | Rush Presbyterian, Chicago, IL (Dr. Coon) | n/a |
| NSCLC292 | Rush Presbyterian, Chicago, IL (Dr. Coon) | n/a |
| NSCLC294 | Rush Presbyterian, Chicago, IL (Dr. Coon) | n/a |
| NSCLC295 | Rush Presbyterian, Chicago, IL (Dr. Coon) | n/a |
| NSCLC296 | Rush Presbyterian, Chicago, IL (Dr. Coon) | n/a |
| NSCLC298 | Rush Presbyterian, Chicago, IL (Dr. Coon) | n/a |
| NSCLC96 | Rush Presbyterian, Chicago, IL (Dr. Coon) | n/a |
| NSCLC97 | Rush Presbyterian, Chicago, IL (Dr. Coon) | n/a |
| NSCLC98 | Rush Presbyterian, Chicago, IL (Dr. Coon) | n/a |
| NSCLC99 | Rush Presbyterian, Chicago, IL (Dr. Coon) | n/a |

Once the tumors and cancer cell lines are obtained, genomic DNA (gDNA) is extracted from each of the tumors or cell lines using routine techniques, such as, phenol-chloroform extraction, salting out, digestion-free extraction or by the use of commercially available kits, such as the DNEasy® or QIAAMP® kits (Qiagen, Valencia, Calif.). The gDNA obtained from each of the tumors or cell lines can then be modified or altered to facilitate analysis. For example, primer or adaptor sequences can be ligated to gDNA using routine techniques. For example, the gDNA can first be digested with a restriction endonuclease, such as HindIII or XbaI. Once digested, one or more primer or adapted sequences can be ligated to the digested gDNA. Preferably, the adaptors are those that recognize cohesive four base-pair overhangs.

The isolated DNA is amplified using routine methods. Useful nucleic acid amplification methods include the Polymerase Chain Reaction (PCR). PCR is described in a number of references (Innis, 1990; Innis et al., 1995; McPherson et al., 1991; Saiki et al., 1986; Sninsky et al., 1999); and U.S. Pat. Nos. 4,683,195, 4,683,202 and 4,889,818, each of which is incorporated herein by reference. Variations of PCR including TAQMAN®-based assays (Holland et al., 1991), and reverse transcriptase polymerase chain reaction (RT-PCR; described in, for example, U.S. Pat. Nos. 5,322,770 and 5,310,652, each of which is incorporated by reference).

Generally, a pair of primers is added to the isolated gDNA to hybridize to the complementary strands of the target nucleic acid. If the gDNA obtained from the tumors or cancer cell lines is digested and ligated to primer or adaptor sequences, then it is preferred that one of the primers used in the amplification method recognize the adaptor sequences. It is also preferred that the primers used in the amplification method amplify fragments in the 250 to 2000 base pair size range.

Upon completion of the amplification, the resulting amplified DNA is purified, using routine techniques, such as MINELUTE® 96 UF PCR Purification system (Qiagen). After purification, the amplified DNA is then fragmented using routine techniques, such as sonication or enzymatic digestion, such as DNase I. After fragmentation, the DNA is labeled with a detectable label. Methods for labeling DNA and fragments of DNA are well-known.

Any of a wide variety of detectable labels can be used. Suitable detectable labels include, but are not limited to, various ligands, radionuclides (e.g., $^{32}P$, $^{35}S$, $^{3}H$, $^{14}C$, $^{125}I$, $^{131}I$, and the like); fluorescent dyes; chemiluminescent agents (e.g., acridinium esters, stabilized dioxetanes, and the like); spectrally resolvable inorganic fluorescent semiconductor nanocrystals (e.g., quantum dots), metal nanoparticles (e.g., gold, silver, copper and platinum) or nanoclusters; enzymes (e.g., horseradish peroxidase, beta-galactosidase, luciferase, alkaline phosphatase); colorimetric labels (e.g., dyes, colloidal gold, and the like); magnetic labels (e.g., DYNABEADS™); and biotin, dioxigenin or other haptens and proteins.

Once the amplified, fragmented DNA is labeled with a detectable label, it is hybridized to a microarray using routine techniques. The microarray can contain oligonucleotides, genes or genomic clones that can be used in Comparative Genomic Hybridization (CGH) to look for genomic gains and losses. Alternatively, the microarray can contain oligonucleotides or genomic clones that detect mutations or polymorphisms, such as single nucleotide polymorphisms (SNPs). Microarrays can be made using routine techniques known in the art. Alternatively, commercially available microarrays can be used. Examples of microarrays that can be used are the AFFYMETRIX® GENECHIP® Mapping 100K Set SNP Array (Matsuzaki et al., 2004) (Affymetrix, Inc., Santa Clara, Calif.), the Agilent Human Genome aCGH Microarray 44B (Agilent Technologies, Inc., Santa Clara, Calif.), Illumina microarrays (Illumina, Inc., San Diego, Calif.), Nimblegen aCGH microarrays (Nimblegen, Inc., Madison, Wis.), etc.

After hybridization, the microarray is washed using routine techniques to remove non-hybridized nucleic acids. After washing, the microarray is analyzed in a reader or scanner. Examples of readers and scanners include GENECHIP® Scanner 3000 G7 (Affymetrix, Inc.), the Agilent DNA Microarray Scanner (Agilent Technologies, Inc.), GENE-PIX® 4000B (Molecular Devices, Sunnyvale, Calif.), etc. Signals gathered from the probes contained in the microarray can be analyzed using commercially available software, such as those provided by Affymetrix or Agilent Technologies. For example, if the GENECHIP® Scanner 3000 G7 from Affymetrix is used, the AFFYMETRIX® GENECHIP® Operating Software can be used. The AFFYMETRIX® GENECHIP® Operating Software collects and extracts the raw or feature data (signals) from the AFFYMETRIX® GENECHIP® scanners that detect the signals from all the probes. The raw or feature data can be stored electronically in one of any suitable file formats, such as a CEL file (the format of the CEL file is an ASCII text file similar to the Windows INI format), a CHP file, a CNT file, a metaprobeset file or a plain text file.

The data collected and extracted from the microarray are processed to determine the copy number at each locus on each chromosome and to define regions of copy number alterations. Such processing can be done using known algorithms, such as Binary Circular segmentation (Olshen et al., 2004), Gain and Loss Analysis of DNA (GLAD) (Hupe et al., 2004), Hidden Markov Model-based approaches (Fridlyand et al., 2004; Zhao et al., 2004), or clustering methods (Wang et al., 2005), etc. Alternatively, commercially available software can be used, such as, the PARTEK® GENOMIC SUITE™ software, such as version 6.08.0103 (available from Partek, St. Louis, Mo.), GenePattern (available on-line; (Reich et al., 2006)), and dChip (available on-line; (Li and Hung Wong, 2001; Li and Wong, 2001).

For example, if the PARTEK® GENOMIC SUITE™ software, such as version 6.08.0103 is used, CEL files containing the signals from all the probes in the microarray detected by the scanners can be loaded into the software. The copy numbers are calculated by comparing the signal intensities for the tumor or cancer cell line samples determined from the microarray to those in a reference or control after correction to a preset baseline (the number used to establish the preset baseline is not critical and is an integer (n), where n is 1 to 100. For example, the preset baseline can be 2). The reference or control used can be a set of normal tissue samples or paired normal tissues from the same patients as the tumor samples measured by the same microarray platform. The reference or control can comprise at least 5 samples, at least 10 samples, at least 15 samples, at least 20 samples, at least 25 samples, at least 30 samples, at least 35 samples, at least 40 samples, at least 45 samples, at least 50 samples, at least 75 samples, at least 100 samples, at least 150 samples, at least 200 samples, etc.

The resulting copy number data is then segmented, and copy number alteration regions are detected in each sample. The segmentation and detection of copy number alteration regions can be obtained using the following control parameters:

(i) a copy number region must contain at least 100 probes;
(ii) the p-value comparing the mean copy number of the copy number region versus the adjacent copy number regions must be less than 0.00001; and
(iii) the signal/noise ratio of the transition must be greater than 0.1.

The copy number alteration regions can be detected when the mean copy numbers in these regions is statistically less than 1.65 (deletion) or greater than 2.65 (gain) with P values below 0.01.

Because tumor samples can contain a significant percentage of normal cells which can dilute the signal of a copy number alteration, a machine learning algorithm can be used to capture the difference between the copy number patterns of tumor and cancer cell line samples and those of normal samples. Such an algorithm can be used to identify and eliminate tumor samples contaminated by normal cells from further analysis. Thus, this algorithm serves as a data quality control and is referred to as a "data quality control algorithm."

The data quality control algorithm involves selecting a subset of samples with the highest number of copy number alteration regions from the tumor and cancer cell line samples as previously described herein (hereinafter the "first sample set"). A normal set of samples is also selected (hereinafter "the second sample set"). These first and second sample sets are used as a training set to develop a machine learning algorithm to classify samples as either being "normal" or "tumor" samples by tuning the parameters of the algorithm to best represent the difference between first and second sample set. The trained classifier is applied to the remaining tumor or cancer cell line samples to assign a score to each sample. This score represents the probability of each sample being contaminated by normal cells. Samples having a contamination probability over 50% are excluded from the subsequent clustering analysis. Machine learning algorithms that can be used for this purpose, include Random Forests (RF) (Breiman, 2001), Support Vector Machine (SVM) (Vapnik, 1995), Recursive-SVM (Zhang et al., 2006), Least-angle regression (LARS) (Efron et al., 2004), etc.

Because copy number data obtained from microarrays tend to be highly dense and noisy, the copy number data can be smoothed to decrease noise level, and reduce dimensionality (also referred to as "dimension reduction") and data complexity. Data smoothing can be done by first detecting significantly gained or deleted copy number regions in each sample using routine techniques. Once such regions are identified, adjacent regions can be merged if they have similar copy number changes and if the distances between these regions are less than 500 kilobases. Then the entire genome can be segmented using the union of break points from all samples in a data set, and the copy number of each segment can be calculated by averaging the copy number of SNPs probes within each segment (Carrasco et al., 2006). Data smoothing can give better resolution of copy number gains and deletions from each sample.

After data smoothing and dimension reduction, the data set is subjected to an unsupervised clustering method to obtain an overview of the relative similarity between each of the tumor and cancer cell line samples and to obtain an estimate (e.g., a rough estimate) of the number of subgroups (which is also referred to herein as r subgroups) that exist in the data thus far. After data smoothing and dimension reduction, unsupervised clustering methods using the Personal linear dissimilarity algorithm are applied to the smoothed tumor and cell line copy number dataset which is referred to as the "Data Set" or V. The clustering patterns can be plotted and visually inspected to derive a range of possible numbers of subgroups, r, in the Data Set (the range of possible numbers of subgroups in the Data Set will be an integer (n) from 1 to 100). Examples of unsupervised clustering methods that can be used include, but are not limited to, hierarchical clustering, Principal Components Analysis (PCA) (Pearson, 1901) or Multidimensional Scaling (MDS) (Borg and Groenen, 2005). The numbers of subgroups (which are each referred to as "r value", where each r value is an integer from 1 to 100) are then used as input in the clustering analysis using genomic Non-negative Matrix Factorization ("gNMF").

In previous applications of gNMF to cluster CGH data (Carrasco et al., 2006; Maher et al., 2006), the algorithm was stopped when the subgroup assignments of tumor or cancer cell line samples did not change after a pre-defined number of steps (e.g., 100). Based on tests with simulated data as well as actual CGH data, it is believed that this criterion stops (e.g., terminates) the gNMF algorithm too early. Therefore, the gNMF algorithm can be modified so that after a selected number of steps (where the selected number of steps is not critical and is an integer (n) from 1 to 1000, such as, for example, 5 steps, 10 steps, 25 steps, 50 steps, 100 steps, 200 steps, etc.) of multiplicative updating, the divergence of the algorithm from the Data Set is calculated using formula (11):

$$D(V \| WH) = \sum_{i=1}^{n} \sum_{j=1}^{m} \left( V_{ij} \log \frac{V_{ij}}{(WH)_{ij}} - V_{ij} + (WH)_{ij} \right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

Using the above formula, the iterative algorithm stops (also referred to herein as the "stop criterion") if the divergence calculated above does not decrease by more than about 0.001% when compared to the divergence calculated for the previous or prior selected number of steps (for example, 100) of multiplicative updating for the algorithm. This modification to the gNMF algorithm has been found to significantly improve the accuracy of the clustering.

Because gNMF is a stochastic procedure, the algorithm can generate different outcomes when started from different initial values. To further improve the performance of the clustering algorithm, a new multiple initiation strategy was developed. For each Data Set, the strategy involves using the above described stop criterion and randomly starting or repeating the gNMF algorithm for a select number of runs (the select number of runs that the algorithm can be randomly started or repeated and is an integer (n) from 1 to 1000, such as for example, 1, 5, 10, 15, 20, 25, 30, 35, 40, 45, 50, 55, 60, 65, 70, 75, 80, 85, 90, 95, 100, 125, 150, 175, 200, 225, 250, 275, 300, 350, etc). Once the algorithm has completed its randomly selected number of runs, the Pearson correlation coefficient matrix of H for the each of these run is calculated using formula (12):

$$C_{i,j} = \rho(H_{,i}, H_{,j}) = \frac{\frac{1}{r-1} \sum_{k} (H_{k,i} - \overline{H_{,i}})(H_{k,j} - \overline{H_{,j}})}{s_{H_{,i}} s_{H_{,j}}} \quad (12)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups (determined previously herein).

Once the Pearson correlation coefficient matrix of H for each run is determined, the correlation matrices are averaged. The final clustering result can be derived by running an unsupervised clustering method (e.g., such as a hierarchical clustering algorithm) using 1 minus the average correlation matrix as the distance matrix and cutting the dendrogram into r subgroups.

For example, if the gNMF algorithm is randomly run 200 times, after the 200 runs, the Pearson correlation coefficient matrix of H from the output of each of the 200 random gNMF runs is calculated using the above described formula. Then the correlation matrices over the 200 runs are then averaged. The final clustering result can be derived by running a hierarchical clustering algorithm using 1 minus the average correlation matrix as the distance matrix and cutting the dendrogram into r subgroups.

Once the final clustering result is obtained, Cophenetic correlation coefficient, Bayesian Information Criterion (BIC) or a combination of the Cophenetic correlation and BIC is then used to select the best model (namely, the best number of clusters and the best assignment of each sample into one of the clusters) most reflective of the distribution of the genetic patterns of these tumor and cell line samples. Lognormal distribution can be used in this analysis as it is widely used to fit DNA copy numbers (Hodgson et al., 2001). To calculate the likelihood, it can be assumed that samples in each cluster came from the same multi-lognormal distribution where the mean copy number of each segment followed a lognormal distribution. If the correlation between segments is weak, independence can be assumed between segments in the calculation. In this instance, the resulting log-likelihood formula (13) is:

$$\ln L = \frac{1}{2} \ln(2\pi) \sum_{i=1}^{r} \sum_{j=1}^{n_i} \sum_{t=1}^{m} \frac{(y_{ijt} - \mu_{it})^2}{2\sigma_{it}^2} \ln(\sigma_{ij}) \quad (13)$$

where r is the number of clusters, $n_i$ is the number of samples in cluster i, m is the number of segments, $y_{ijt}$ is the log transformed copy number of the $i^{th}$ segment of the $j^{th}$ sample in the $i^{th}$ cluster, $\mu_{it}$ is the average of log transformed copy numbers of the $i^{th}$ segment in the $i^{th}$ cluster, and $\sigma_{it}$ is the standard deviation of log transformed copy numbers of the $i^{th}$ segment in the $i^{th}$ cluster. Then the number of parameters, k, in the specified model would be 2×r×m.

Many times, when using both Cophenetic correlation coefficient and BIC as a criterion to select the best model in unsupervised clustering, these two algorithms will often select the same model.

A 10-fold stability test procedure can be used to assess the stability of the clustering results. The 10-fold stability test can be performed as follows. After running gNMF on the data set and assigning the samples to clusters, at least about 10% of the tumor and cancer cell line samples are left out and the modified gNMF algorithm described above is run a second time on the remaining 90% of the tumor and cancer cell line samples (if at least about 15% of the tumor and cancer cell line samples are left out then the gNMF algorithm described above would be run a second time on the remaining 85% of the tumor and cancer cell line samples, etc.). The number of samples assigned to a different cluster as a result of this permutation is then calculated. The test is repeated a selected number of times (the test can be repeated from 1 to 1000 times. For example, the test can be repeated, 1 time, 20 times, 25 times, 50 times, 100 times, 200 times, 500 times, 750 times, 1000 times, etc.) to derive an error rate using routine techniques known in the art. This error rate represents the stability of the clustering result with respect to the permutation of the tumor and cancer cell line samples. This 10-fold stability test can be used on unsupervised clustering methods (e.g., hierarchical clustering) using the same data sets (the tumor and cancer cell line samples).

Using these methods, tumors harboring NSCLC cells and NSCLC cell lines can be classified into genomic subgroups. First, a sufficient number of NSCLC tumors and NSCLC cell lines are clustered into distinct subgroups using the methodology described above. From each of these subgroups, at least one cell line from each of subgroup is selected and added to the panel, with each panel thus comprising a genomic subgroup. The resulting panel thus adequately represents all genomic subtypes of NSCLC. This panel can be used as pre-clinical models for pharmaceutical composition or drug testing for NSCLC, thus providing comprehensive coverage of the genomic diversity of the tumor type under consideration.

Applications

Having a diagnostic panel assembled allows for increased sensitivity for NSCLC diagnosis. Not only can a subject now be diagnosed for NSCLC, but the subject can also be diagnosed for a "genomic type" of NSCLC based on the classification of the subject's NSCLC genotype in the classification panel. In this way, targeted therapeutic interventions can be administered that increase the success of treatment and improve the quality of life for a subject.

In diagnostic methods of the invention, a sample suspected of containing at least one NSCLC cell is obtained. The cells in the sample are then subjected to microarray analyses, using the same probes and parameters that are used to establish the original diagnostic panel, or any other set of probes and parameters that can detect copy number alterations, and the data set from the microarray analyses is processed so as to determine which subgroup the subject's NSCLC genotype resembles. The subject's NSCLC genotype is then assigned to that subgroup.

From the subgroup information, therapeutic intervention and trials can be designed. For example, as data becomes available on treatment success as related to NSCLC genotypes, a subject can be administered those treatments that have the highest probability of treating NSCLC based on the subjects NSCLC genotype and subgroup classification. In this way, trail-and-error treatment is greatly diminished, as is reliance on the most invasive treatments (surgeries), and the subject has a better chance of both remission and a higher quality of life during treatment. The subject's quality of life improves because treatment periods and the number of therapeutic interventions are decreased.

If treatments are not established, therapeutic interventions can be determined by using the cell panel data. For example, if cell lines L, U, N, G, and S fall into a single subgroup, they can be subjected to in vitro tests of various therapeutic options for potentially efficacy. Those therapeutic interventions that are effective in having an adverse effect on the most cell lines in a cluster represent those interventions most likely to effectively treat the subject.

Therapeutic interventions for NSCLC include invasive surgeries (wedge resection, lobectomy, pneumonectomy, and sleeve resection), radiation therapy (including radiosurgery), chemotherapy, laser therapy, photodynamic therapy (administration of pharmaceutical compositions that are then locally activated by light), biologic therapy (boosting the immune system of a subject to fight NSCLC), and simple "watchful waiting." Chemotherapeutic interventions include administering erlotinib, gefitinib, alimta, cisplatin, gemcitabine, paclitaxel, vinorelbine, epirubicin, vindosine, lonidamine, ifosfamide, carboplatin, and docetaxel, or combinations thereof. Combinations include cisplatin and epirubicin, vindesine and lonidamine, vindesine and cisplatin, gemcitabine, cisplatin and vinorelbine, paclitaxel and ifosfamide, vinorelbine and ifosfamide, gemcitabine and vineorelbine, paclitaxe and carboplatin; and finally, paclitaxel and gemcitabine (Clegg et al., 2002).

Representative cell lines and tumor samples can be subjected to an in vitro test assaying the ability of a therapeutic intervention to treat NSCLC. For example, the cell lines can be assayed for their susceptibility to the various chemotherapy agents, singly and in combinations. When a plurality of cell lines responds similarly to one or more interventions, then those are selected for administration to the subject. Thus, the cell panels can be augmented by in vitro, and eventually, real-world treatment data, providing a therapeutic matrix based on NSCLC copy number profiles.

In another embodiment, the methods of the invention are directed to assembling a probe panel for classifying NSCLC cells. The database of genomic sub-groups is analyzed for most characteristic copy number abnormalities for each subgroup, and probes are designed to detect those regions. The probes can be a subset of the probes used in the original microarray analysis procedure, or designed and optimized for particular characteristics. In one embodiment, such probes are FISH probes. In another embodiment, such probe panels are provided in kits.

In other embodiments, kits are provided for classifying a NSCLC cell that contains, for example, instructions for assembling a database that classifies NSCLC cells by genomic subgroup and at least a first, second and third cell line, or isolated genomic DNA thereof, wherein each cell line or gDNA represents a genomic subgroup. For example, the first cell line or gDNA can be HCC827, NCI-H1437, NCI-H1563, NCI-H1568, NCI-H1623, NCI-H1651, NCI-H1693, NCI-H1755, NCI-H1793, NCI-H1838, NCI-H1944, NCI-H1975, NCI-H1993, NCI-H2023, NCI-H2073, NCI-H2085, NCI-H2087, NCI-H2122, NCI-H2126, NCI-H2228, NCI-H2291, NCI-H23, NCI-H2342, NCI-H2347, NCI-H647, NCI-H920, NCI-H969, CLS-54, LX-289, SK-LU-1, H2882, Calu-6, H358, and H460; the second cell line or gDNA can be NCI-H2405, NCI-H522, SK-MES-1, H157, H1819, H2009, H2887, HCC1171, HCC1359, HCC15, HCC193, HCC366, HCC461, HCC515, HCC78, HOP-62, HOP-92, and NCI-H266; and the third cell line or gDNA can be A549, Calu-3, NCI-H1734, NCI-H838, and HCC95. Kits can include probe panels, as well as control cell lines or gDNA that are normal or not NSCLC cells.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

The methods of the invention directed to NSCLC classification are summarized in FIG. 1.

Example 1

Cell Lines and Tissue Samples

The inventors used 57 cell lines and 245 tumor samples to establish a NSCLC classification model. The sources of cell lines and tumors used in this study are listed in Table 1, above. Tumor samples were procured from a variety of sources.

Example 2

Step 1: DNA Extraction and Hybridization to SNPs Arrays

The AFFYMETRIX® GENECHIP® Mapping 100K Set SNP array (Matsuzaki et al., 2004) (Affymetrix, Inc., Santa Clara, Calif.) covers 116,204 single-nucleotide polymorphism (SNP) loci in the human genome with a mean intermarker distance of 23.6 kb. The array set includes two chips, Xba240 and Hind240. The assays were carried out according to the manufacturer's instructions. Briefly, high molecular weight, genomic DNA was extracted from 30 mg tissue from each tumor or 5×10$^6$ cells from each cell line using a QIAGEN® DNEASY® kit (Qiagen, Valencia, Calif.). Two-hundred fifty nanograms of genomic DNA were digested with either HindIII or XbaI. Adaptors (XbaI, 5' tctagagatc aggcgtctgt cgtgctcata a 3'; SEQ ID NO:2; HindIII, 5' acgta-gatca ggcgtctgtc gtgctcataa 3'; SEQ ID NO:3) were then ligated to the digested fragments that recognize the cohesive four base-pair (bp) overhangs. A generic primer that recognizes the adaptor sequence (5' attatgagca cgacagacgc ctgatct 3' SEQ ID NO:1) was used to amplify adaptor-ligated DNA fragments with PCR conditions optimized to preferentially amplify fragments in the 250-2,000 by size range in a GENE-AMP® PCR System 9700 (Applied Biosystems, Foster City, Calif.). After purification with a MINELUTE® 96 UF PCR purification system (Qiagen), the PCR product was fragmented, labeled with biotin and hybridized to the GENECHIP® Mapping 100K Set for 16 hours. The arrays were washed using the Fluidics Station F-450 (Affymetrix) and scanned using a GENECHIP® Scanner 3000 G7 (Affymetrix). The GENECHIP® operating software (GCOS) collected and extracted feature data from GENECHIP® scanners.

Copy number data can also be acquired using other SNPs or CGH microarray platforms, such as other versions of AFFYMETRIX® SNPs microarrays, Agilent aCGH microarrays (Agilent, Inc., Santa Clara, Calif.), ILLUMINA® microarrays (Illumina, Inc., San Diego, Calif.), and NIMBLEGEN® aCGH microarrays (Nimblegen, Inc., Madison, Wis.).

Example 3

Step 2: Copy Number Determination and Detection of Copy Number Alterations

Genomic Suite software (version 6.08.0103) (Partek; St. Louis, Mo.) was used for low-level processing of the data to determine the copy numbers of each locus and define regions of copy number alteration. CEL files containing signals for all SNPs probes were loaded into the software, and copy numbers were calculated by comparing the signal intensities for tumor or cell line samples to those for a reference set of 48 normal female tissue samples, corrected to a baseline of 2. The reference set can also consist of other sets of normal samples, or paired normal tissues from the same patients of the tumor samples, measured by the same microarray platform.

The resulting probe-level copy number data were segmented, and the copy number alteration regions were detected in each sample. Specifically, probe-level copy numbers were segmented into regions using the following control parameters: (i) a region must contain at least 100 probes, (ii) the p-value comparing the mean copy number of the region versus the adjacent regions must be less than 0.00001, and (iii) the signal/noise ratio of the transition must be greater than 0.1. The copy number alteration regions were detected when the mean copy numbers in these regions were less than 1.65 (deletion) or greater than 2.65 (gain) with P values below 0.01.

The segmentation of copy number and detection of copy number alterations can also be achieved by other algorithms, such as the Binary Circular segmentation (Olshen et al., 2004), Gain and Loss Analysis of DNA (GLAD) (Hupe et al., 2004), Hidden Markov Model-based approaches (Fridlyand et al., 2004) (Zhao et al., 2004), or clustering methods (Wang et al., 2005), etc. These methods have been implemented in several software packages such as GenePattern (Reich et al., 2006) and dChip (Li and Hung Wong, 2001; Li and Wong, 2001).

Example 4

Step 3: Data Quality Control

Tumor samples may contain a significant percentage of normal cells that dilute the signal of copy number alteration present in the tumor cells. A machine learning algorithm to capture the difference between copy number patterns of tumor and normal samples was developed and then used to identify and eliminate normal contaminated samples from further analyses. First, a subset of samples with the highest number of copy number alteration regions and a set of normal samples were selected. These two groups of samples were used to train a machine learning algorithm (Random Forest: RF (Breiman, 2001)) to classify normal and tumor samples by tuning the parameters to best represent the difference between tumor and normal samples. Second, the trained classifier algorithm was applied to the rest of samples; the classifier assigned a score to each sample, where the score represented the probability of the sample being contaminated by normal cells. Samples that had a probability score of over 50% normal cell contamination were excluded from clustering analysis.

Example 5

Step 4: Data Smoothing and Dimension Reduction

The density of copy number data obtained by SNPs microarrays was high and there was a significant amount of noise. Consequently, copy number data was smoothed to reduce noise, dimensionality and complexity of the clustering analysis. After detecting significantly gained or deleted regions in each sample, adjacent regions were merged if they had similar copy number changes and the distance between them was less than 500 kb. The DNA segments were formed by using the union of break points from all samples in a data set. The average copy number of probes within each segment was used for further analysis. This step allowed for a clearer resolution of DNA gains and deletions in the high-throughput analysis.

Example 6

Step 5: Pilot Clustering Analysis Using Hierarchical Clustering to Determine the Possible Number of Subgroups For each data set, the inventors hierarchically clustered the tumor and cell line CGH data using Pearson dissimilarity (defined as $(1-r)/2$, where r is the Pearson correlation). The hierarchical clustering patterns were plotted and visually inspected to derive a range of possible numbers of subgroups in the dataset. These numbers were then used as input in the clustering analysis using genomic Non-negative Matrix Factorization.

Example 7

Step 6: gNMF Clustering of the Tumor and Cell Line CGH Data

The gNMF algorithm was used to classify the tumor and cell line CGH data, using cluster numbers range determined in step 5. With each cluster number, the gNMF algorithm was run 200 times using the stop criterion we developed. Classification models were then derived by hierarchical clustering on 1 minus the average of correlation matrix of H.

Example 8

Step 7: Model Selection Using Cophenetic Correlation and Bayesian Information Criterion (BIC)

The above gNMF procedure was run with several possible r values (number of subgroups) chosen in the initial hierarchical clustering analysis, and several models with different numbers of subgroups were built. The Cophenetic correlation coefficient and Bayesian Information Criterion (BIC) were then used to select the best model (the number of subgroups and the assignment of each sample into one of the subgroups) that best reflected the distribution of the genetic patterns of the tumor and cell line samples.

Both Cophenetic correlation coefficient and BIC were used as a criterion to select the model that best reflected the distribution of the genetic patterns of the tumor and cell line samples in the unsupervised clustering. It was found that these two criteria often point at the same model. After choosing the best model, each of the NSCLC tumor samples and cell lines was assigned to one of the genomic subgroups based on the selected model. Additional NSCLC tumor samples profiled in the future can also be assigned to one of the subgroups based on their genomic pattern.

Example 9

Step 8: Ten-Fold Stability Test of Clustering Stability

A 10-fold stability test procedure was developed to assess the stability of the classification results. After running gNMF on a data set and assigning tumor and cell line samples to subgroups, 10% of samples were randomly left out, and the same procedure was applied to the remaining 90% of samples. The number of samples that were assigned to a different subgroup by this permutation was calculated. This leave-out test was repeated 200 times to derive an error rate, which represents the stability of the clustering result with respect to permutation of samples. The stability of hierarchical clustering using the same procedure for the same data sets was also assessed and found that it was always much higher than that of gNMF clustering.

Example 10

Results

Steps 1-2. The 302 NSCLC tumor and cell line samples were prepared, and the data were processed as described in Examples 2 and 3. A total of 11419 segments with a significantly altered copy number were detected.

Step 3. The data quality control procedure was applied to the NSCLC CGH data. No tumor samples were found to be significantly contaminated by normal cells. All samples were used in the analysis.

Step 4. The dimensionality of the CGH data was reduced to 8172 segments.

Figure 2:
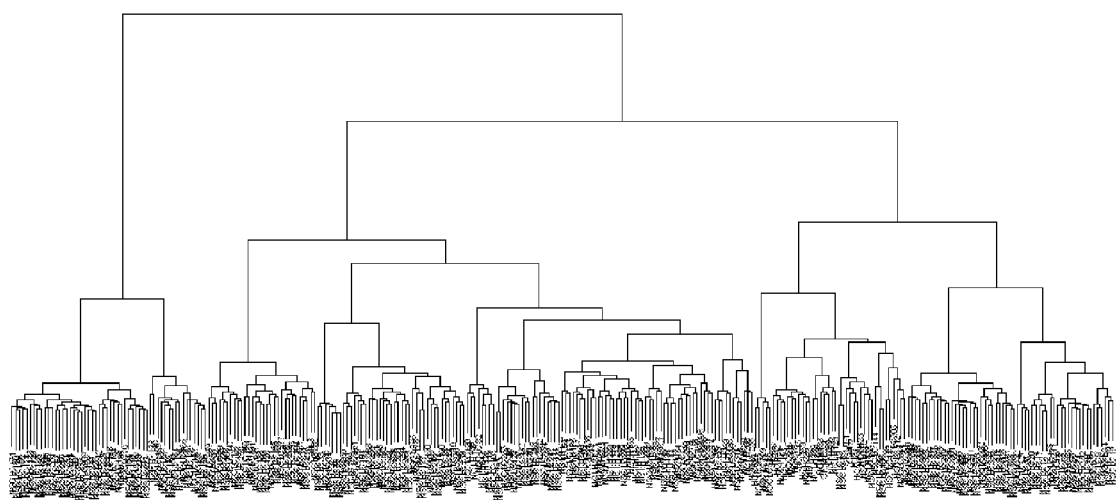
FIG. 2 shows a dendrogram of the NSCLC data set in order to derive the possible number of clusters generated by using hierarchical clustering.

Step 5. Hierarchical clustering was used as an initial analysis on the NSCLC data set to estimate the number of clusters. The dendrogram of the clustering is shown in FIG. 2. Visual inspection of the dendrogram suggested the existence of 3-8 major clusters in the data.

Step 6. The gNMF algorithm was used to classify the tumor and cell line CGH data, using cluster numbers in the range of 3-8. With each cluster number, the gNMF algorithm was run 200 times using the stop criterion we developed. Classification models were then derived by hierarchical clustering on 1 minus the average of correlation matrix of H.

Figure 3:
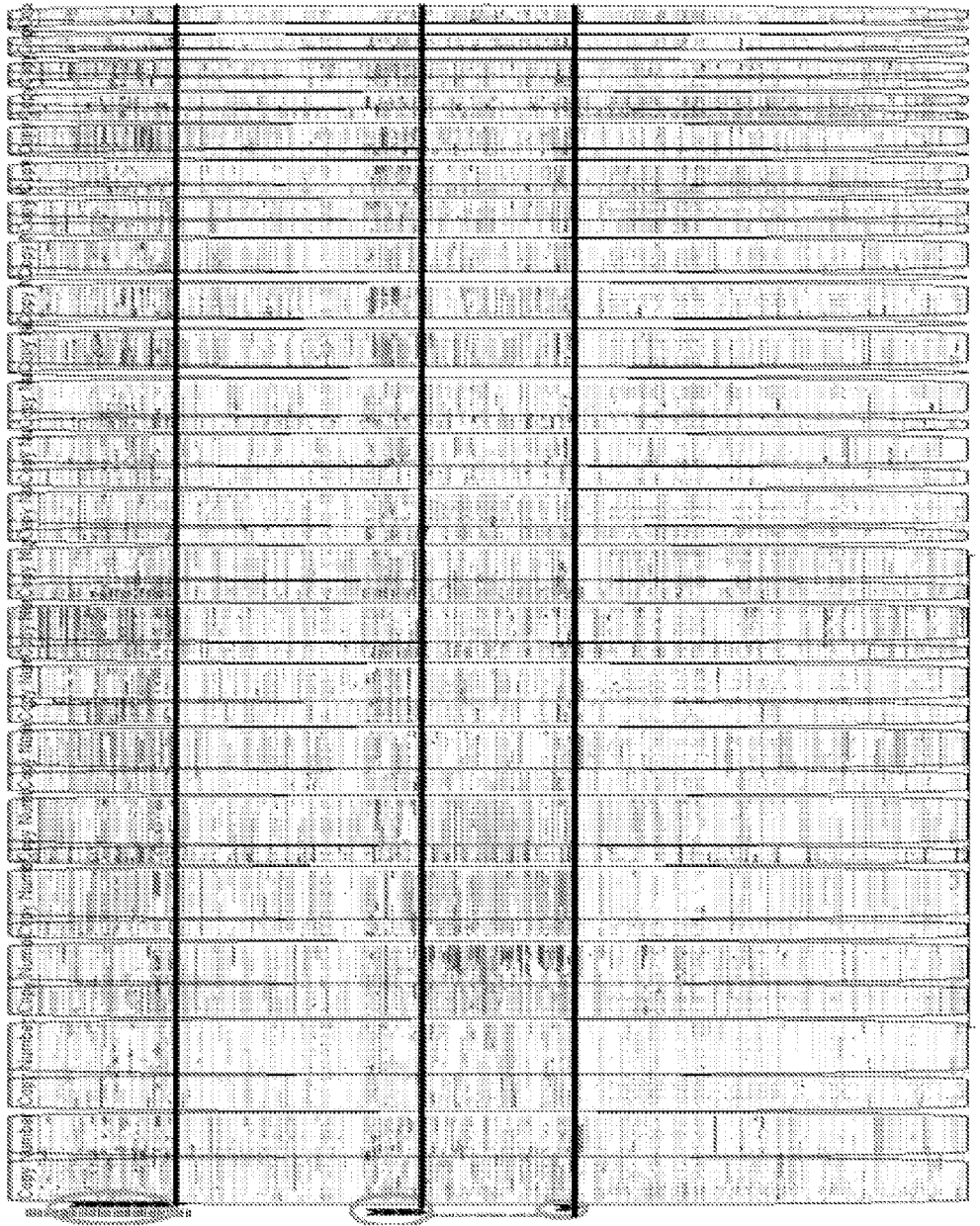
FIG. 3 shows a heatmap of the NSCLC tumor and cell line CGH data as classified into 4 clusters by genomic Non-negative Matrix Factorization (gNMF). Each row represents a sample, and each column represents a SNP locus; red, white and blue colors indicate high, normal and low copy numbers, respectively; horizontal black lines separate different genomic subgroups; vertical spaces separate chromosome 1 to 22; cell lines are highlighted by green circles.

Step 7. The Cophenetic correlation and BIC were calculated for the gNMF models fitted in step 6. The results are listed in Table 2, where r denotes the number of clusters in each model. From the results shown in Table 2, the inventors found that the model with 4 clusters had the smallest BIC, and that between cluster numbers 4 and 5, the Cophenetic correlation showed the greatest decrease. Therefore, 4 clusters was the best choice for this data set. The heatmap of the gNMF output with 4 clusters is shown in FIG. 3.

TABLE 2

Cophenetic correlation and BIC for models using different cluster numbers

| r | Cophenetic correlation | BIC |
|---|---|---|
| 3 | 0.8031 | 1032670 |
| 4 | 0.7664 | 992443 |
| 5 | 0.7103 | 1249580 |
| 6 | 0.7166 | 1301055 |
| 7 | 0.7040 | 1301808 |
| 8 | 0.7109 | 1202876 |

The 245 NSCLC tumor samples were classified into 4 subgroups based on their pattern of copy number alterations, and cell lines were assigned to appropriate subgroups. The numbers of tumor samples and the identities of cell lines for each cluster are listed in Table 3.

TABLE 3

Numbers of NSCLC tumors and the identities of cell lines in each subgroup of NSCLC

| Clusters | Number of tumors | Cell Lines |
|---|---|---|
| Cluster A | 19 | HCC827, NCI-H1437, NCI-H1563, NCI-H1568, NCI-H1623, NCI-H1651, NCI-H1693, NCI-H1755, NCI-H1793, NCI-H1838, NCI-H1944, NCI-H1975, NCI-H1993, NCI-H2023, NCI-H2073, NCI-H2085, NCI-H2087, NCI-H2122, NCI-H2126, NCI-H2228, NCI-H2291, NCI-H23, NCI-H2342, NCI-H2347, NCI-H647, NCI-H920, NCI-H969, CLS-54, LX-289, SK-LU-1, H2882, Calu-6, H358, H460 |

TABLE 3-continued

Numbers of NSCLC tumors and the identities of cell lines in each subgroup of NSCLC

| Clusters | Number of tumors | Cell Lines |
|---|---|---|
| Cluster B | 60 | NCI-H2405, NCI-H522, SK-MES-1, H157, H1819, H2009, H2887, HCC1171, HCC1359, HCC15, HCC193, HCC366, |
| Cluster C | 42 | HCC461, HCC515, HCC78, HOP-62, HOP-92, NCI-H266 |
| Cluster D | 124 | A549, Calu-3, NCI-H1734, NCI-H838, HCC95 |

Step 8. The 10-fold stability test was applied to the gNMF model with 4 clusters. The error rate was 14.24%. As a comparison, the hierarchical clustering dendrogram derived using the smoothed copy number data in step 5 into 3-8 clusters was cut, and the stability of the clusters using the same 10-fold test was tested. The error rates were 19.45%-25.65%, much higher than that of the gNMF model.

The four subgroups defined by the clustering procedure carried distinct patterns of genomic aberrations, implying different origins and tumorigenic mechanisms. This observation suggests that the different subgroups will manifest distinct clinical behaviors and sensitivities to therapeutic interventions, characteristic of each subgroup.

Example 11

Validation of the Genomic Clustering Results Using Outcome-Annotated Tumor Samples To determine whether the NSCLC genomic clusters identified have biologically meaningful differences, two sets of tumor samples were used with disease outcome annotation. Two outcome parameters were used, time to recurrence (TTR) and overall survival (OS).

Figure 4:
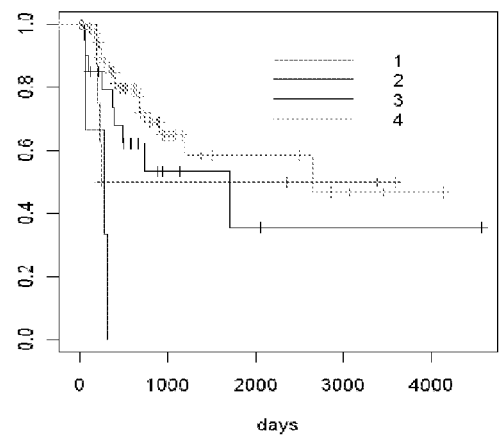
FIG. 4 shows Kaplan-Meier curve of the time to recurrence (TTR) for clinically annotated samples in the four NSCLC clusters: (a) four clusters considered separately; and (b) clusters 1 and 2 combined.
Figure 4:
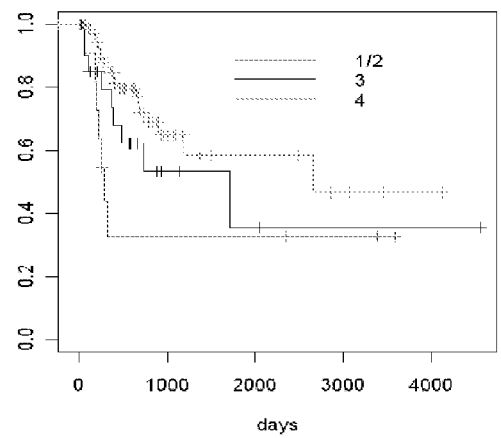

Among the 245 NSCLC tumor samples used in NSCLC classification (See, Example 1), disease outcome information (overall survival and time to recurrence) was available for 111 samples collected at Rush University Medical Center, Chicago, Ill. The numbers of outcome-annotated samples in clusters 1, 2, 3, and 4 were 9, 3, 21 and 78, respectively. A logrank test comparing their TTRs showed a significant P-value of 0.0006. Since there were only three samples in cluster 2, an effort was made to combine samples in cluster 1 and cluster 2 together. The combined samples had significantly lower TTR than the other 2 clusters with P-value of 0.0397. The Kaplan-Meier curves are shown in FIG. 4.

To further validate the unsupervised clustering algorithm for cancer classification based on copy number alterations, and the cell line models selected to represent different subgroups of cancer patients, an additional study using 71 NSCLC tumor samples (Table 4, below) was used with associated outcome information.

TABLE 4

Validation samples and sources

| Sample ID | Source |
|---|---|
| SML-007 | Samsung Medical Center, Seoul, Korea (Dr. Kim) |
| SML-008 | Samsung Medical Center, Seoul, Korea (Dr. Kim) |
| SML-012 | Samsung Medical Center, Seoul, Korea (Dr. Kim) |
| SML-013 | Samsung Medical Center, Seoul, Korea (Dr. Kim) |
| SML-014 | Samsung Medical Center, Seoul, Korea (Dr. Kim) |
| SML-019 | Samsung Medical Center, Seoul, Korea (Dr. Kim) |
| SML-047 | Samsung Medical Center, Seoul, Korea (Dr. Kim) |
| SML-048 | Samsung Medical Center, Seoul, Korea (Dr. Kim) |

TABLE 4-continued

Validation samples and sources

| Sample ID | Source |
|---|---|
| SML-053 | Samsung Medical Center, Seoul, Korea (Dr. Kim) |
| SML-070 | Samsung Medical Center, Seoul, Korea (Dr. Kim) |
| SML-071 | Samsung Medical Center, Seoul, Korea (Dr. Kim) |
| SML-083 | Samsung Medical Center, Seoul, Korea (Dr. Kim) |
| SML-086 | Samsung Medical Center, Seoul, Korea (Dr. Kim) |
| SML-093 | Samsung Medical Center, Seoul, Korea (Dr. Kim) |
| SML-094 | Samsung Medical Center, Seoul, Korea (Dr. Kim) |
| SML-095 | Samsung Medical Center, Seoul, Korea (Dr. Kim) |
| SML-096 | Samsung Medical Center, Seoul, Korea (Dr. Kim) |
| SML-103 | Samsung Medical Center, Seoul, Korea (Dr. Kim) |
| SML-107 | Samsung Medical Center, Seoul, Korea (Dr. Kim) |
| SML-110 | Samsung Medical Center, Seoul, Korea (Dr. Kim) |
| SML-111 | Samsung Medical Center, Seoul, Korea (Dr. Kim) |
| SML-118 | Samsung Medical Center, Seoul, Korea (Dr. Kim) |
| SML-119 | Samsung Medical Center, Seoul, Korea (Dr. Kim) |
| SML-120 | Samsung Medical Center, Seoul, Korea (Dr. Kim) |
| SML-122 | Samsung Medical Center, Seoul, Korea (Dr. Kim) |
| SML-123 | Samsung Medical Center, Seoul, Korea (Dr. Kim) |
| SML-137 | Samsung Medical Center, Seoul, Korea (Dr. Kim) |
| SML-138 | Samsung Medical Center, Seoul, Korea (Dr. Kim) |
| SML-141 | Samsung Medical Center, Seoul, Korea (Dr. Kim) |
| SML-142 | Samsung Medical Center, Seoul, Korea (Dr. Kim) |
| SML-143 | Samsung Medical Center, Seoul, Korea (Dr. Kim) |
| SML-144 | Samsung Medical Center, Seoul, Korea (Dr. Kim) |
| SML-176 | Samsung Medical Center, Seoul, Korea (Dr. Kim) |
| SML-192 | Samsung Medical Center, Seoul, Korea (Dr. Kim) |
| SML-198 | Samsung Medical Center, Seoul, Korea (Dr. Kim) |
| SML-209 | Samsung Medical Center, Seoul, Korea (Dr. Kim) |
| SML-231 | Samsung Medical Center, Seoul, Korea (Dr. Kim) |
| SML-232 | Samsung Medical Center, Seoul, Korea (Dr. Kim) |
| SML-237 | Samsung Medical Center, Seoul, Korea (Dr. Kim) |
| SML-239 | Samsung Medical Center, Seoul, Korea (Dr. Kim) |
| SML-244 | Samsung Medical Center, Seoul, Korea (Dr. Kim) |
| SML-055 | Samsung Medical Center, Seoul, Korea (Dr. Kim) |
| SML-088 | Samsung Medical Center, Seoul, Korea (Dr. Kim) |
| SML-018 | Samsung Medical Center, Seoul, Korea (Dr. Kim) |
| SML-021 | Samsung Medical Center, Seoul, Korea (Dr. Kim) |
| SML-024 | Samsung Medical Center, Seoul, Korea (Dr. Kim) |
| SML-028 | Samsung Medical Center, Seoul, Korea (Dr. Kim) |
| SML-029 | Samsung Medical Center, Seoul, Korea (Dr. Kim) |
| SML-030 | Samsung Medical Center, Seoul, Korea (Dr. Kim) |
| SML-031 | Samsung Medical Center, Seoul, Korea (Dr. Kim) |
| SML-033 | Samsung Medical Center, Seoul, Korea (Dr. Kim) |
| SML-035 | Samsung Medical Center, Seoul, Korea (Dr. Kim) |
| SML-037 | Samsung Medical Center, Seoul, Korea (Dr. Kim) |
| SML-039 | Samsung Medical Center, Seoul, Korea (Dr. Kim) |
| SML-040 | Samsung Medical Center, Seoul, Korea (Dr. Kim) |
| SML-041 | Samsung Medical Center, Seoul, Korea (Dr. Kim) |
| SML-044 | Samsung Medical Center, Seoul, Korea (Dr. Kim) |
| SML-062 | Samsung Medical Center, Seoul, Korea (Dr. Kim) |
| SML-064 | Samsung Medical Center, Seoul, Korea (Dr. Kim) |
| SML-067 | Samsung Medical Center, Seoul, Korea (Dr. Kim) |
| SML-068 | Samsung Medical Center, Seoul, Korea (Dr. Kim) |
| SML-079 | Samsung Medical Center, Seoul, Korea (Dr. Kim) |
| SML-080 | Samsung Medical Center, Seoul, Korea (Dr. Kim) |
| SML-091 | Samsung Medical Center, Seoul, Korea (Dr. Kim) |
| SML-092 | Samsung Medical Center, Seoul, Korea (Dr. Kim) |
| SML-099 | Samsung Medical Center, Seoul, Korea (Dr. Kim) |
| SML-100 | Samsung Medical Center, Seoul, Korea (Dr. Kim) |
| SML-105 | Samsung Medical Center, Seoul, Korea (Dr. Kim) |
| SML-116 | Samsung Medical Center, Seoul, Korea (Dr. Kim) |

TABLE 4-continued

Validation samples and sources

| Sample ID | Source |
|---|---|
| SML-147 | Samsung Medical Center, Seoul, Korea (Dr. Kim) |
| SML-203 | Samsung Medical Center, Seoul, Korea (Dr. Kim) |

The samples were processed, DNA were extracted, amplified and hybridized to Affymetrix SNP 6.0 arrays following Affymetrix experimental protocols (See, Examples 2-3). Copy number of these tumors was calculated by comparing to HapMap set of 270 normal controls. The copy number was segmented using Partek software 6.09.0310 (See, Example 3).

To assign the validation samples to the four NSCLC clusters, Pearson correlation coefficients of the outcome-annotated tumor samples were calculated for each of the representative cell lines of the first three clusters (See Examples 4-9). Since the $4^{th}$ cluster did not have representative cell line, all tumor samples in the $4^{th}$ cluster were used as its representatives and calculated their Pearson correlation coefficient to the validation samples. The validation samples were then assigned to the cluster that contained the representative cell line or tumor that has the highest correlation coefficient with the validation sample. Finally, the differences in TTR and OS of the validation samples assigned into different clusters were compared using a logrank test and plotted their Kaplan-Meier curves (See, Examples 4-9).

Figure 5:
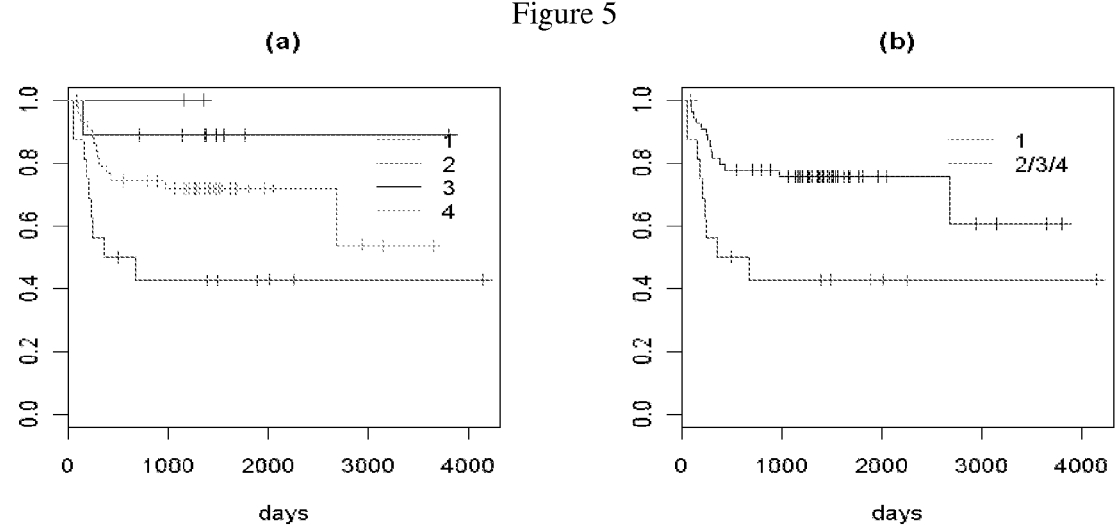
FIG. 5 shows Kaplan-Meier curve of the TTR for the validation samples assigned into the four clusters: (a) four clusters considered separately; and (b) cluster 1 compared with the remaining three clusters.

The difference in TTR between the four clusters is significant with a P-value of 0.0454 for the validation samples. Furthermore, the Kaplan-Meier curve showed a significantly lower TTR for samples in cluster 1 relative to the other clusters (See, FIG. 5). If samples in clusters 2, 3, and 4 are combined and compared to the samples in cluster 1, the P-value is 0.0094.

Figure 6:
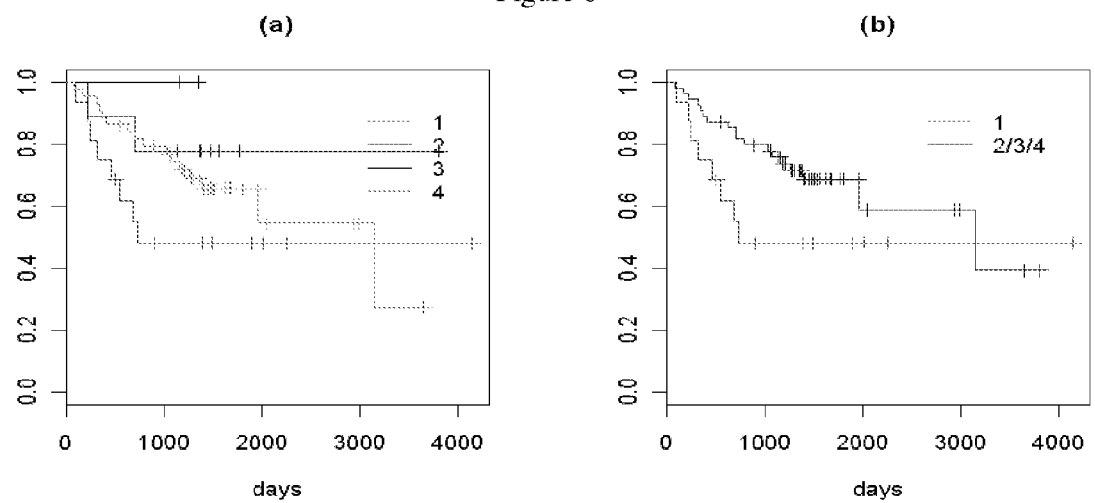
FIG. 6 shows Kaplan-Meier curve of the Overall Survival (OS) between the validation samples assigned into the four clusters: (a) four clusters considered separately; and (b) cluster 1 compared with the remaining three clusters.

The difference in OS between the 4 clusters was not significant (P-value=0.25) for the validation samples, but the Kaplan-Meier curve showed a trend of lower OS for samples in cluster 1 relative to the other clusters (See, FIG. 6). If samples in clusters 2, 3, and 4 are combined and compared to samples in cluster 1, the P-value is marginally significant (P-value=0.116).

Figure 7:
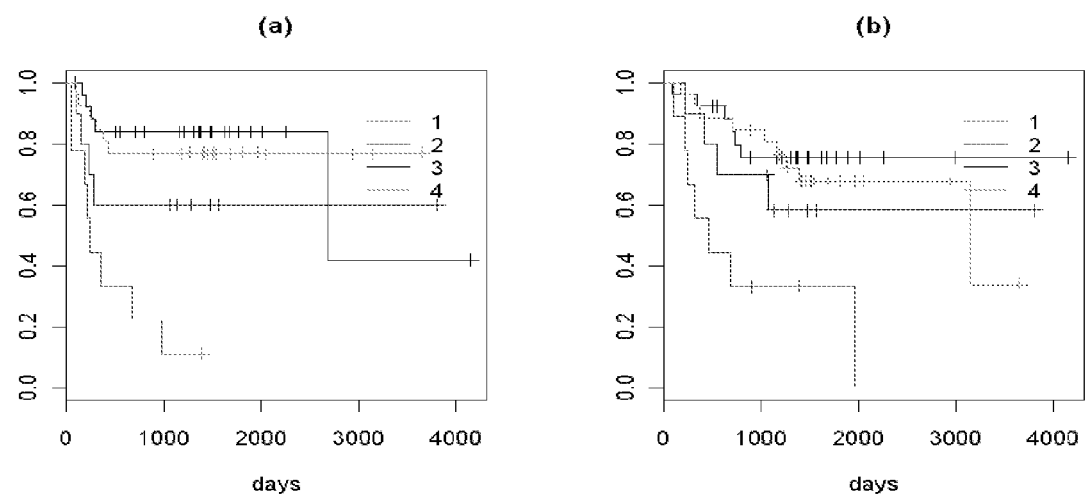
FIG. 7 shows Kaplan-Meier curve of the TTR and OS between the validation samples assigned into the four clusters using all existing tumor and cell lines to represent the clusters: (a) TTR; and (b) OS.

Alternatively, all tumors and cell lines in our already defined clusters was used to represent the clusters and assigned the validation samples to the four clusters by the highest Pearson correlation coefficient between the validation samples and the existing samples. In this analysis, both TTR and OS showed significant differences between the four clusters with P-values of 4.7E-5 and 0.0024, respectively. Samples assigned to cluster 1 had a significantly lower TTR and OS than samples assigned to other clusters (See, FIG. 7).

To conclude, outcome-annotated samples were used in the data set as well as independent samples to determine whether the NSCLC genomic clusters identified have biologically meaningful differences. The results show that the clusters differ significantly in time to recurrence and overall survival of patients, indicating that the genomic classification correlates with differences in the disease course, and the cell lines representing different clusters can be used as models to predict different clinical outcomes.

REFERENCES

Anand, S., S. Penrhyn-Lowe, and A. R. Venkitaraman. 2003. AURORA-A amplification overrides the mitotic spindle assembly checkpoint, inducing resistance to Taxol. *Cancer Cell*. 3:51-62.

Ausubel, F. M. 1987. Current protocols in molecular biology. Greene Publishing Associates; J. Wiley, order fulfillment, Brooklyn, N.Y. Media, Pa. 2 v. (loose-leaf) pp.

Bhattacharjee, A., W. G. Richards, J. Staunton, C. Li, S. Monti, P. Vasa, C. Ladd, J. Beheshti, R. Bueno, M. Gillette, M. Loda, G. Weber, E. J. Mark, E. S. Lander, W. Wong, B. E. Johnson, T. R. Golub, D. J. Sugarbaker, and M. Meyerson. 2001. Classification of human lung carcinomas by mRNA expression profiling reveals distinct adenocarcinoma subclasses. *Proc Natl Acad Sci USA*. 98:13790-5.

Borg, I., and P. Groenen. 2005. Modern Multidimensional Scaling: theory and applications. Springer, New York.

Breiman, L. 2001. Random Forests. *Machine Learning*. 45:5-32.

Brunet, J. P., P. Tamayo, T. R. Golub, and J. P. Mesirov. 2004. Metagenes and molecular pattern discovery using matrix factorization. *Proc Natl Acad Sci USA*. 101:4164-9.

Carrasco, D. R., G. Tonon, Y. Huang, Y. Zhang, R. Sinha, B. Feng, J. P. Stewart, F. Zhan, D. Khatry, M. Protopopova, A. Protopopov, K. Sukhdeo, I. Hanamura, O. Stephens, B. Barlogie, K. C. Anderson, L. Chin, J. D. Shaughnessy, Jr., C. Brennan, and R. A. Depinho. 2006. High-resolution genomic profiles define distinct clinico-pathogenetic subgroups of multiple myeloma patients. *Cancer Cell*. 9:313-25.

Clegg, A., D. A. Scott, P. Hewitson, M. Sidhu, and N. Waugh. 2002. Clinical and cost effectiveness of paclitaxel, docetaxel, gemcitabine, and vinorelbine in non-small cell lung cancer: a systematic review. *Thorax*. 57:20-8.

Efron, B., T. Hastie, I. Johnstone, and R. Tibshirani. 2004. Least angle regression. *Annals of Statistics*. 32:407-499.

Fodor, S. P., J. L. Read, M. C. Pirrung, L. Stryer, A. T. Lu, and D. Solas. 1991. Light-directed, spatially addressable parallel chemical synthesis. *Science*. 251:767-73.

Fridlyand, J., A. M. Snijders, D. Pinkel, D. G. Albertson, and A. N. Jain. 2004. Hidden Markov models approach to the analysis of array CGH data. *Journal of Multivariate Analysis*. 90:132-153.

Hedenfalk, I., M. Ringner, A. Ben-Dor, Z. Yakhini, Y. Chen, G. Chebil, R. Ach, N. Loman, H. Olsson, P. Meltzer, A. Borg, and J. Trent. 2003. Molecular classification of familial non-BRCA1/BRCA2 breast cancer. *Proc Natl Acad Sci USA*. 100:2532-7.

Hirsch, F. R., M. Varella-Garcia, P. A. Bunn, Jr., W. A. Franklin, R. Dziadziuszko, N. Thatcher, A. Chang, P. Parikh, J. R. Pereira, T. Ciuleanu, J. von Pawel, C. Watkins, A. Flannery, G. Ellison, E. Donald, L. Knight, D. Parums, N. Botwood, and B. Holloway. 2006. Molecular predictors of outcome with gefitinib in a phase III placebo-controlled study in advanced non-small-cell lung cancer. *J Clin Oncol*. 24:5034-42.

Hodgson, G., J. H. Hager, S. Volik, S. Hariono, M. Wernick, D. Moore, N. Nowak, D. G. Albertson, D. Pinkel, C. Collins, D. Hanahan, and J. W. Gray. 2001. Genome scanning with array CGH delineates regional alterations in mouse islet carcinomas. *Nat Genet*. 29:459-64.

Hoffman, P. C., A. M. Mauer, and E. E. Vokes. 2000. Lung cancer. *Lancet*. 355:479-85.

Holland, P. M., R. D. Abramson, R. Watson, and D. H. Gelfand. 1991. Detection of specific polymerase chain reaction product by utilizing the 5' - - - 3' exonuclease activity of *Thermus aquaticus* DNA polymerase. *Proc Natl Acad Sci USA*. 88:7276-80.

Hupe, P., N. Stransky, J. P. Thiery, F. Radvanyi, and E. Barillot. 2004. Analysis of array CGH data: from signal ratio to gain and loss of DNA regions. *Bioinformatics*. 20:3413-22.

Innis, M. A. 1990. PCR protocols: a guide to methods and applications. Academic Press, San Diego. xviii, 482 p. pp.

Innis, M. A., D. H. Gelfand, and J. J. Sninsky. 1995. PCR strategies. Academic Press, San Diego. xv, 373 p. pp.

Lee, D. D., and H. S. Seung. 1999. Learning the parts of objects by non-negative matrix factorization. *Nature*. 401: 788-91.

Lee, D. D., and H. S. Seung. 2001. Algorithms for Non-negative Matrix Factorization. *Advances In Neural Information Processing Systems*. 14:556-562.

Levsky, J. M., and R. H. Singer. 2003. Fluorescence in situ hybridization: past, present and future. *J Cell Sci*. 116: 2833-8.

Li, C., and W. Hung Wong. 2001. Model-based analysis of oligonucleotide arrays: model validation, design issues and standard error application. *Genome Biol*. 2:RESEARCH0032.

Li, C., and W. H. Wong. 2001. Model-based analysis of oligonucleotide arrays: expression index computation and outlier detection. *Proc Natl Acad Sci USA*. 98:31-6.

Maher, E. A., C. Brennan, P. Y. Wen, L. Durso, K. L. Ligon, A. Richardson, D. Khatry, B. Feng, R. Sinha, D. N. Louis, J. Quackenbush, P. M. Black, L. Chin, and R. A. DePinho. 2006. Marked genomic differences characterize primary and secondary glioblastoma subtypes and identify two distinct molecular and clinical secondary glioblastoma entities. *Cancer Res*. 66:11502-13.

Matsuzaki, H., S. Dong, H. Loi, X. Di, G. Liu, E. Hubbell, J. Law, T. Berntsen, M. Chadha, H. Hui, G. Yang, G. C. Kennedy, T. A. Webster, S. Cawley, P. S. Walsh, K. W. Jones, S. P. Fodor, and R. Mei. 2004. Genotyping over 100,000 SNPs on a pair of oligonucleotide arrays. *Nat Methods*. 1:109-11.

McPherson, M. J., G. R. Taylor, and P. Quirke. 1991. PCR, a practical approach. IRL Press at Oxford University Press, Oxford; New York. xxi, 253 p. pp.

Olshen, A. B., E. S. Venkatraman, R. Lucito, and M. Wigler. 2004. Circular binary segmentation for the analysis of array-based DNA copy number data. *Biostatistics*. 5:557-72.

Parkin, D. M. 2001. Global cancer statistics in the year 2000. *Lancet Oncol*. 2:533-43.

Pearson, K. 1901. On Lines and Planes of Closest Fit to Systems of Points in Space. *Philosophical Magazine*. 2:559-572.

Reich, M., T. Liefeld, J. Gould, J. Lerner, P. Tamayo, and J. P. Mesirov. 2006. GenePattern 2.0. *Nat Genet*. 38:500-1.

Ross, D. T., U. Scherf, M. B. Eisen, C. M. Perou, C. Rees, P. Spellman, V. Iyer, S. S. Jeffrey, M. Van de Rijn, M. Waltham, A. Pergamenschikov, J. C. Lee, D. Lashkari, D. Shalon, T. G. Myers, J. N. Weinstein, D. Botstein, and P. O. Brown. 2000. Systematic variation in gene expression patterns in human cancer cell lines. *Nat Genet*. 24:227-35.

Saiki, R. K., T. L. Bugawan, G. T. Horn, K. B. Mullis, and H. A. Erlich. 1986. Analysis of enzymatically amplified beta-globin and HLA-DQ alpha DNA with allele-specific oligonucleotide probes. *Nature*. 324:163-6.

Sambrook, J., and D. W. Russell. 2001. Molecular cloning: a laboratory manual. Cold Spring Harbor Laboratory Press, Cold Spring Harbor, N.Y.

Seeger, R. C., G. M. Brodeur, H. Sather, A. Dalton, S. E. Siegel, K. Y. Wong, and D. Hammond. 1985. Association of multiple copies of the N-myc oncogene with rapid progression of neuroblastomas. *N Engl J Med*. 313:1111-6.

Sninsky, J. J., M. A. Innis, and D. H. Gelfand. 1999. PCR applications: protocols for functional genomics. Academic Press, San Diego. xviii, 566 p., [3] p. of plates pp.

Sotiriou, C., S. Y. Neo, L. M. McShane, E. L. Korn, P. M. Long, A. Jazaeri, P. Martiat, S. B. Fox, A. L. Harris, and E. T. Liu. 2003. Breast cancer classification and prognosis based on gene expression profiles from a population-based study. *Proc Natl Acad Sci USA*. 100:10393-8.

Travis, W. D., and L. H. Sobin. 1999. Histological typing of lung and pleural tumours. Springer-Verlag, Berlin; N.Y. xii, 156 p. pp.

Vapnik, V. 1995. The nature of statistical learning theory. Springer-Verlag, New York.

Vogel, C. L., M. A. Cobleigh, D. Tripathy, J. C. Gutheil, L. N. Harris, L. Fehrenbacher, D. J. Slamon, M. Murphy, W. F. Novotny, M. Burchmore, S. Shak, S. J. Stewart, and M. Press. 2002. Efficacy and safety of trastuzumab as a single agent in first-line treatment of HER2-overexpressing metastatic breast cancer. *J Clin Oncol*. 20:719-26.

Wang, P., Y. Kim, J. Pollack, B. Narasimhan, and R. Tibshirani. 2005. A method for calling gains and losses in array CGH data. *Biostatistics*. 6:45-58.

Wilhelm, M., J. A. Veltman, A. B. Olshen, A. N. Jain, D. H. Moore, J. C. Presti, Jr., G. Kovacs, and F. M. Waldman. 2002. Array-based comparative genomic hybridization for the differential diagnosis of renal cell cancer. *Cancer Res*. 62:957-60.

Zhang, X., X. Lu, Q. Shi, X. Q. Xu, H. C. Leung, L. N. Harris, J. D. Iglehart, A. Miron, J. S. Liu, and W. H. Wong. 2006. Recursive SVM feature selection and sample classification for mass-spectrometry and microarray data. *BMC Bioinformatics*. 7:197.

Zhao, X., C. Li, J. G. Paez, K. Chin, P. A. Janne, T. H. Chen, L. Girard, J. Minna, D. Christiani, C. Leo, J. W. Gray, W. R. Sellers, and M. Meyerson. 2004. An integrated view of copy number and allelic alterations in the cancer genome using single nucleotide polymorphism arrays. *Cancer Res*. 64:3060-71.

Zhao, X., B. A. Weir, T. LaFramboise, M. Lin, R. Beroukhim, L. Garraway, J. Beheshti, J. C. Lee, K. Naoki, W. G. Richards, D. Sugarbaker, F. Chen, M. A. Rubin, P. A. Janne, L. Girard, J. Minna, D. Christiani, C. Li, W. R. Sellers, and M. Meyerson. 2005. Homozygous deletions and chromosome amplifications in human lung carcinomas revealed by single nucleotide polymorphism array analysis. *Cancer Res*. 65:5561-70.

We claim:

1. A method of classifying a therapeutic intervention for arresting or killing non-small cell lung carcinoma (NSCLC) cells, comprising:
   (a) from a panel of NSCLC cells classified according to genomic subgroups, selecting at least one NSCLS cell line from each subgroup, wherein the panel is assembled from a method comprising:
      (i) obtaining a plurality of m samples comprising at least one NSCLC tumor or cell line;
      (ii) acquiring a first data set comprising copy number alteration information from at least one locus from each chromosome from each sample obtained in step (i);
      (iii) identifying in the first data set samples contaminated by normal cells and eliminating the contaminated samples from the first data set, wherein the identifying and eliminating comprises:
         (1) applying a machine learning algorithm tuned to parameters that represent the differences between tumor and normal samples to the data;
         (2) assigning a probability score for normal cell contamination to each sample as determined by the machine learning algorithm;
         (3) eliminating data from the first data set for each sample scoring 50% or greater probability of being contaminated by normal cells;
      (iv) estimating a range of a number of subgroups, r, in the data set by applying an unsupervised clustering algorithm using Pearson linear dissimilarity algorithm to the data set, to generate a dendrogram;
      (v) assigning each sample in the data set to at least one subgroup using a modified genomic Non-negative Matrix Factorization (gNMF) algorithm with each one of the values within the range estimated in step (iv), wherein the modified gNMF algorithm comprises:
         (1) calculating divergence of the gNMF algorithm after every 100 steps of one run of multiplicative updating of the gNMF algorithm using formula (11):

$$D(V \| WH) = \sum_{i=1}^{n} \sum_{j=1}^{m} \left( V_{ij} \log \frac{V_{ij}}{(WH)_{ij}} - V_{ij} + (WH)_{ij} \right) \quad (11)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of DNA segments in the data set, and j runs from 1 to m and m is the number of samples in the data set;

(2) stopping the gNMF algorithm if the divergence calculated in step (v)(1) does not decrease by more than about 0.001% when compared to the divergence calculated for the previous 100 steps of multiplicative updating of the gNMF algorithm;
   (3) repeating the gNMF algorithm for a randomly selected number of runs, each with a random start point, and calculating a Pearson correlation coefficient matrix of H for each run of the gNMF algorithm using formula (12):

$$C_{i,j} = \rho(H_{\cdot,i}, H_{\cdot,j}) = \frac{\frac{1}{r-1} \sum_{k} (H_{k,i} - \overline{H_{\cdot,i}})(H_{k,j} - \overline{H_{\cdot,j}})}{s_{H_{\cdot,i}} s_{H_{\cdot,j}}} \quad (12)$$

wherein C is the correlation matrix, $C_{i,j}$ is the $i^{th}$ row and $j^{th}$ column in the matrix C, $H_{\cdot,i}$ and $H_{\cdot,j}$ are the $i^{th}$ and $j^{th}$ column vector in matrix H, $\rho(H_{\cdot,i}, H_{\cdot,j})$ is the Pearson correlation coefficient between $H_{\cdot,i}$ and $H_{\cdot,j}$, i and j run from 1 to m and m is the number of samples in the data set, k runs from 1 to r and r is the number of subgroups from step (iv);
(4) averaging the Pearson correlation coefficient matrices for each run of the gNMF algorithm obtained from step (v)(3) to arrive at an average correlation matrix;
(5) assigning the tumors and cell lines in the data set into r subgroups by applying an unsupervised clustering algorithm using the identity matrix minus the average correlation matrix determined in step (v)(4) and cutting the dendrogram into r subgroups;
(vi) applying a Cophenetic correlation, Bayesian Information Criterion, or a combination thereof to provide a final number of subgroups from the data set, wherein each final subgroup defines a genomic subgroup for each sample;
(vii) optionally evaluating the stability of the final number of subgroups selected in step (vi) using a ten-fold stability test;
(viii) selecting at least one NSCLC cell from each subgroup selected in step (vi) and assembling into panels defined according to genomic subgroups;
(b) contacting the at least one NSCLC cell from each subgroup with the therapeutic intervention;
(c) assaying the effectiveness of the therapeutic intervention to arrest or kill the at least one NSCLC cell from each subgroup;
(d) classifying the therapeutic intervention according to the determined effectiveness of the therapeutic intervention to arrest or kill the at least one NSCLC cell from each subgroup,
wherein the plurality of samples, m, consists of CLS-54, LX-289, SK-LU-1, SK-MES-1, H157, H1819, H2009, H2882, H2887, HCC1171, HCC1359, HCC15, HCC193, HCC366, HCC461, HCC515, HCC78, HCC95, HOP-62, HOP-92, NCI-H266, NCIH1437, NCI-H1563, NCI-H1568, NCI-H1623, NCI-H1651, NCI-H1693, NCI-H1734, NCI-H1755, NCI-H1793, NCI-H1838, NCI-H1944, NCI-H1975, NCI-H1993, NCI-H2023, NCI-H2073, NCIH2085, NCI-H2087, NCI-H2122, NCI-H2126, NCI-H2228, NCI-H2291, NCI-H23, NCI-H2342, NCI-H2347, NCI-H2405, NCI-H522, NCI-H647, NCI-H838, NCI-H920, NCI-H969, A549, Calu-3, HCC827, Calu-6, H358 and H460 cell lines,
wherein arresting or killing the at least one NSCLC cell from one subgroup, but not another indicates specificity of the therapeutic intervention to arrest or kill NSCLC cells of that subgroup.

2. The method of claim 1, wherein the unsupervised clustering algorithm is a hierarchical clustering.

3. The method of claim 1, wherein Cophenetic correlation is used to provide a final number of subgroups from the data set.

4. The method of claim 1, wherein Bayesian Information Criterion is used to provide a final number of subgroups from the data set.

5. The method of claim 1, wherein Cophenetic correlation and Bayesian Information Criterion are used to provide a final number of subgroups from the data set.

6. The method of claim 1, wherein the NSCLC cells are from a cell line.

7. The method of claim 1, wherein the therapeutic intervention comprises at least one selected from the group consisting of radiation therapy, chemotherapy, laser therapy, photodynamic, and biologic therapy.

8. The method of claim 7, wherein the therapeutic intervention is chemotherapy, and the chemotherapy comprises administering at least one pharmaceutical composition comprising an active agent selected from the group consisting of erlotinib, gefitinib, alimta, cisplatin, gemcitabine, paclitaxel, vinorelbine, epirubicin, vindesine, lonidamine, ifosfamide, carboplatin, and docetaxel and ifosfamide.

9. The method of claim 8, wherein the chemotherapy comprises administering two or more active agents.

\* \* \* \* \*

SEQUENCE LISTING

```
<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 1
attatgagca cgacagacgc ctgatct                                          27

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctagagatc aggcgtctgt cgtgctcata a                                     31

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgtagatca ggcgtctgtc gtgctcataa                                       30
```